US006132964A

United States Patent [19]
Bandman et al.

[11] Patent Number: 6,132,964
[45] Date of Patent: Oct. 17, 2000

[54] HYDROLASE ENZYMES

[75] Inventors: Olga Bandman, Mountain View; Preeti Lal, Santa Clara; Jennifer L. Hillman; Neil C. Corley, both of Mountain View; Karl J. Guegler, Menlo Park; Purvi Shah, Sunnyvale, all of Calif.

[73] Assignee: Incyte Pharmaceuticals, Inc., Palo Alto, Calif.

[21] Appl. No.: 09/013,881

[22] Filed: Feb. 6, 1998

[51] Int. Cl.[7] .............................. C12Q 1/68; C07H 21/04; C12N 1/20; C12N 15/63

[52] U.S. Cl. .......................... 435/6; 435/69.1; 435/71.1; 435/320.1; 435/455; 435/471; 435/195; 435/252.3; 536/23.5; 536/23.2; 536/24.31; 536/24.33

[58] Field of Search .......................... 435/6, 91.2, 320.1, 435/455, 471, 195, 252.3, 69.1, 71.1; 536/23.5, 24.31, 24.33, 23.2

[56] References Cited

U.S. PATENT DOCUMENTS 5,801,031   9/1998   Galivan et al. ........................ 435/172.3

OTHER PUBLICATIONS

Hillier et al. GenBank Accession No. AA478657, Aug. 1997.
Hillier et al. GenBank Accession No. W73220, Oct. 1996.
Hillier et al. GenBank Accession No. N31113, Jan. 1996.
Hillier et al. GenBank Accession No. AA147450, Dec. 1996.
Hillier et al. GenBank Accession No. AA056327, Feb. 1997.
Hillier et al. GenBank Accession No. H17385, Jun. 1995.
Adams et al. GenBank Accession No. AA308083, Apr. 1997.
NCI–CGAP, GenBank Accession No. AA595667, Sep. 1997.
Hillier et al. GenBank Accession No. W76203, Oct. 1996.
Li, M. et al. "Purification and Characterization of Two Potent Heat–Stable Protein Inhibitors of Protein Phosphatase 2A from Bovine Kidney", *Biochemistry*, 34: 1988–1996 (1995).
Selle, H. et al. "Glycerophosphocholine release in human erythrocytes 1H spin–echo and $^{31}$P–NMR evidence for lysophospholipase", *Eur. J. Biochem.*, 212: 411–416 (1993).
Thornalley, P.J. "Modification of the glyoxalase system in disease processes and prospects for therapeutic strategies", *Biochemical Society Transactions*, 21: 531–534 (1993).
Thornalley, P.J. "The Glyoxalase System in Health and Disease" *Molec. Aspects Med.*, 14: 287–371 (1993).
Frearson, J.A. and Denis R. Alexander, "The role of phosphotyrosine phosphatases in haematopoietic cell signal transduction", *BioEssays*, 19: 417–427 (1997).
Goldstein, B.J. "Protein–Tyrosine Phosphatases and the Regulation of Insulin Action", *J. Cell. Biochem.*, 48: 33–42 (1992).
Wilson, R. et al., (Direct Submission), GenBank Sequence Database (Accession 1938421), National Center for Biotechnology Information, National Library of Medicine, Bethesda, Maryland, 20894, GI 1938421), 1997.
Wilson, R. et al., (Direct Submission), GenBank Sequence Database (Accession 1938421), National Center for Biotechnology Information, National Library of Medicine, Bethesda, Maryland, 20894, (GI 1938421), 1997.
Kawasaki, K. et al., (Direct Submission), GenBank Sequence Database (Accession 2114221), National Center for Biotechnology Information, National Library of Medicine, Bethesda, Maryland, 20894, (GI 2114221), 1997.
Kawasaki, K. et al., (Direct Submission), GenBank Sequence Database (Accession D86995), National Center for Biotechnology Information, National Library of Medicine, Bethesda, Maryland, 20894, (GI 211422; GI 2114221), 1997.
Guan, K. et al., (Direct Submission), GenBank Sequence Database (Accession 172168), National Center for Biotechnology Information, National Library of Medicine, Bethesda, Maryland, 20894, (GI 172168), 1993.
Guan, K. et al., (Direct Submission), GenBank Sequence Database (Accession L04673), National Center for Biotechnology Information, National Library of Medicine, Bethesda, Maryland, 20894, (GI 172167; GI 172168), 1993.
Ishibashi, T. et al., (Direct Submission), GenBank Sequence Database (Accession 181840), National Center for Biotechnology Information, National Library of Medicine, Bethesda, Maryland, 20894, (GI 181840), 1993.
Ishibashi, T. et al., (Direct Submission), GenBank Sequence Database (Accession L05147), National Center for Biotechnology Information, National Library of Medicine, Bethesda, Maryland, 20894, (GI 181839; GI 181840), 1993.
Hofman, K. (Direct Submission), GenBank Sequence Database (Accession 1552350), National Center for Biotechnology Information, National Library of Medicine, Bethesda, Maryland, 20894, (GI 1552350), 1996.
Hofman, K. (Direct Submission), GenBank Sequence Database (Accession Y08135), National Center for Biotechnology Information, National Library of Medicine, Bethesda, Maryland, 20894, (GI 1552349; GI 1552350), 1996.
Wilson, R. et al., (Direct Submission), GenBank Sequence Database (Accession 1938421), National Center for Biotechnology Information, National Library of Medicine, Bethesda, Maryland, 20894, (GI 1938421), 1997.
Wilson, R. et al., (Direct Submission), GenBank Sequence Database (Accession U97001), National Center for Biotechnology Information, National Library of Medicine, Bethesda, Maryland, 20894, (GI 1938418; GI 1938421), 1997.

(List continued on next page.)

*Primary Examiner*—Carla J. Myers
*Attorney, Agent, or Firm*—Incyte Pharmaceuticals, Inc.; Matthew R. Kaser

[57] ABSTRACT

The invention provides human hydrolase-like molecules (HHLM) and polynucleotides which identify and encode HHLM. The invention also provides expression vectors, host cells, antibodies, agonists, and antagonists. The invention also provides methods for treating or preventing disorders associated with expression of HHLM.

17 Claims, No Drawings

OTHER PUBLICATIONS

Wang, A. et al., (Direct Submission), GenBank Sequence Database (Accession 1864159), National Center for Biotechnology Information, National Library of Medicine, Bethesda, Maryland, 20894, (GI 1864159), 1997.

Wang, A. et al., (Direct Submission), GenBank Sequence Database (Accession U89352), National Center for Biotechnology Information, National Library of Medicine, Bethesda, Maryland, 20894, (GI 1864158; GI 1864159), 1996.

Wintz, H. and W. Sakamoto, (Direct Submission), GenBank Sequence Database (Accession 1644427), National Center for Biotechnology Information, National Library of Medicine, Bethesda, Maryland, 20894, (GI 1644427), 1996.

Wintz, H. and W. Sakamoto, (Direct Submission), GenBank Sequence Database (Accession U74610), National Center for Biotechnology Information, National Library of Medicine, Bethesda, Maryland, 20894, (GI 1644426; GI 1644427), 1996.

SEQUENCE LISTING (1) GENERAL INFORMATION:

(iii) NUMBER OF SEQUENCES:16

(2) INFORMATION FOR SEQ ID NO: 1:

(i) SEQUENCE CHARACTERISTICS:
      (A) LENGTH: 259 amino acids
      (B) TYPE: amino acid
      (C) STRANDEDNESS: single
      (D) TOPOLOGY: linear (vii) IMMEDIATE SOURCE:
      (A) LIBRARY: PITUNOT01
      (B) CLONE: 094168

(xi) SEQUENCE DESCRIPTION: SEQ ID NO: 1 :

```
Met Ala Ala Cys Arg Ala Leu Lys Ala Val Leu Val Asp Leu Ser
                 5                  10                  15

Gly Thr Leu His Ile Glu Asp Ala Ala Val Pro Gly Ala Gln Glu
                20                  25                  30

Ala Leu Lys Arg Leu Arg Gly Ala Ser Val Ile Ile Arg Phe Val
                35                  40                  45

Thr Asn Thr Thr Lys Glu Ser Lys Gln Asp Leu Leu Glu Arg Leu
                50                  55                  60

Arg Lys Leu Glu Phe Asp Ile Ser Glu Asp Glu Ile Phe Thr Ser
                65                  70                  75

Leu Thr Ala Ala Arg Ser Leu Leu Glu Arg Lys Gln Val Arg Pro
                80                  85                  90

Met Leu Leu Val Asp Asp Arg Ala Leu Pro Asp Phe Lys Gly Ile
                95                 100                 105

Gln Thr Ser Asp Pro Asn Ala Val Val Met Gly Leu Ala Pro Glu
               110                 115                 120

His Phe His Tyr Gln Ile Leu Asn Gln Ala Phe Arg Leu Leu Leu
               125                 130                 135

Asp Gly Ala Pro Leu Ile Ala Ile His Lys Ala Arg Tyr Tyr Lys
               140                 145                 150

Arg Lys Asp Gly Leu Ala Leu Gly Pro Gly Pro Phe Val Thr Ala
               155                 160                 165

Leu Glu Tyr Ala Thr Asp Thr Lys Ala Thr Val Val Gly Lys Pro
               170                 175                 180

Glu Lys Thr Phe Phe Leu Glu Ala Leu Arg Gly Thr Gly Cys Glu
               185                 190                 195

Pro Glu Glu Ala Val Met Ile Gly Asp Asp Cys Arg Asp Asp Val
               200                 205                 210

Gly Gly Ala Gln Asp Val Gly Met Leu Gly Ile Leu Val Lys Thr
               215                 220                 225

Gly Lys Tyr Arg Ala Ser Asp Glu Glu Lys Ile Asn Pro Pro Pro
               230                 235                 240

Tyr Leu Thr Cys Glu Ser Phe Pro His Ala Val Asp His Ile Leu
               245                 250                 255

Gln His Leu Leu
```

(2) INFORMATION FOR SEQ ID NO: 2:

(i) SEQUENCE CHARACTERISTICS:

(A) LENGTH: 392 amino acids
(B) TYPE: amino acid
(C) STRANDEDNESS: single
(D) TOPOLOGY: linear (vii) IMMEDIATE SOURCE:
(A) LIBRARY: KIDNNOT02
(B) CLONE: 195647

(xi) SEQUENCE DESCRIPTION: SEQ ID NO: 2 :

```
Met Asp Leu Phe Gly Asp Leu Pro Glu Pro Glu Arg Ser Pro Arg
                  5                  10                  15

Pro Ala Ala Gly Lys Glu Ala Gln Lys Gly Pro Leu Leu Phe Asp
                 20                  25                  30

Asp Leu Pro Pro Ala Ser Ser Thr Asp Ser Gly Ser Gly Gly Pro
                 35                  40                  45

Leu Leu Phe Asp Asp Leu Pro Pro Ala Ser Ser Gly Asp Ser Gly
                 50                  55                  60

Ser Leu Ala Thr Ser Ile Ser Gln Met Val Lys Thr Glu Gly Lys
                 65                  70                  75

Gly Ala Lys Arg Lys Thr Ser Glu Glu Lys Asn Gly Ser Glu
                 80                  85                  90

Glu Leu Val Glu Lys Lys Val Cys Lys Ala Ser Ser Val Ile Phe
                 95                 100                 105

Gly Leu Lys Gly Tyr Val Ala Glu Arg Lys Gly Glu Arg Glu Glu
                110                 115                 120

Met Gln Asp Ala His Val Ile Leu Asn Asp Ile Thr Glu Glu Cys
                125                 130                 135

Arg Pro Pro Ser Ser Leu Ile Thr Arg Val Ser Tyr Phe Ala Val
                140                 145                 150

Phe Asp Gly His Gly Gly Ile Arg Ala Ser Lys Phe Ala Ala Gln
                155                 160                 165

Asn Leu His Gln Asn Leu Ile Arg Lys Phe Pro Lys Gly Asp Val
                170                 175                 180

Ile Ser Val Glu Lys Thr Val Lys Arg Cys Leu Leu Asp Thr Phe
                185                 190                 195

Lys His Thr Asp Glu Glu Phe Leu Lys Gln Ala Ser Ser Gln Lys
                200                 205                 210

Pro Ala Trp Lys Asp Gly Ser Thr Ala Thr Cys Val Leu Ala Val
                215                 220                 225

Asp Asn Ile Leu Tyr Ile Ala Asn Leu Gly Asp Ser Arg Ala Ile
                230                 235                 240

Leu Cys Arg Tyr Asn Glu Glu Ser Gln Lys His Ala Ala Leu Ser
                245                 250                 255

Leu Ser Lys Glu His Asn Pro Thr Gln Tyr Glu Glu Arg Met Arg
                260                 265                 270

Ile Gln Lys Ala Gly Gly Asn Val Arg Asp Gly Arg Val Leu Gly
                275                 280                 285

Val Leu Glu Val Ser Arg Ser Ile Gly Asp Gly Gln Tyr Lys Arg
                290                 295                 300

Cys Gly Val Thr Ser Val Pro Asp Ile Arg Arg Cys Gln Leu Thr
                305                 310                 315

Pro Asn Asp Arg Phe Ile Leu Leu Ala Cys Asp Gly Leu Phe Lys
                320                 325                 330

Val Phe Thr Pro Glu Glu Ala Val Asn Phe Ile Leu Ser Cys Leu
                335                 340                 345
```

```
Glu Asp Glu Lys Ile Gln Thr Arg Glu Gly Lys Ser Ala Ala Asp
                350                 355                 360

Ala Arg Tyr Glu Ala Ala Cys Asn Arg Leu Ala Asn Lys Ala Val
            365                 370                 375

Gln Arg Gly Ser Ala Asp Asn Val Thr Val Met Val Val Arg Ile
        380                 385                 390

Gly His
```

(2) INFORMATION FOR SEQ ID NO:    3:

(i) SEQUENCE CHARACTERISTICS:
        (A) LENGTH: 353 amino acids
        (B) TYPE: amino acid
        (C) STRANDEDNESS: single
        (D) TOPOLOGY: linear (vii) IMMEDIATE SOURCE:
        (A) LIBRARY: TMLR3DT02
        (B) CLONE: 507537

(xi) SEQUENCE DESCRIPTION: SEQ ID NO: 3 :

```
Met Val Gly Gln Glu Ala Ala Leu Ser Leu Gly Ala Ala Met Leu
                5                  10                  15

Glu Ala Pro Gly Pro Ser Asp Gly Cys Glu Leu Ser Asn Pro Ser
            20                  25                  30

Ala Ser Arg Val Ser Cys Ala Gly Gln Met Leu Glu Val Gln Pro
        35                  40                  45

Gly Leu Tyr Phe Gly Gly Ala Ala Val Ala Glu Pro Asp His
    50                  55                  60

Leu Arg Glu Ala Gly Ile Thr Ala Val Leu Thr Val Asp Ser Glu
                65                  70                  75

Glu Pro Ser Phe Lys Ala Gly Pro Gly Val Glu Asp Leu Trp Arg
            80                  85                  90

Leu Phe Val Pro Ala Leu Asp Lys Pro Glu Thr Asp Leu Leu Ser
        95                  100                 105

His Leu Asp Arg Cys Val Ala Phe Ile Gly Gln Ala Arg Ala Glu
                110                 115                 120

Gly Arg Ala Val Leu Val His Cys His Ala Gly Val Ser Arg Ser
            125                 130                 135

Val Ala Ile Ile Thr Ala Phe Leu Met Lys Thr Asp Gln Leu Pro
        140                 145                 150

Phe Glu Lys Ala Tyr Glu Lys Leu Gln Ile Leu Lys Pro Glu Ala
                155                 160                 165

Lys Met Asn Glu Gly Phe Glu Trp Gln Leu Lys Leu Tyr Gln Ala
            170                 175                 180

Met Gly Tyr Glu Val Asp Thr Ser Ser Ala Ile Tyr Lys Gln Tyr
        185                 190                 195

Arg Leu Gln Lys Val Thr Glu Lys Tyr Pro Glu Leu Gln Asn Leu
                200                 205                 210

Pro Gln Glu Leu Phe Ala Val Asp Pro Thr Thr Val Ser Gln Gly
            215                 220                 225

Leu Lys Asp Glu Val Leu Tyr Lys Cys Arg Lys Cys Arg Arg Ser
        230                 235                 240

Leu Phe Arg Ser Ser Ser Ile Leu Asp His Arg Glu Gly Ser Gly
                245                 250                 255

Pro Ile Ala Phe Ala His Lys Arg Met Thr Pro Ser Ser Met Leu
```

```
                    260                 265                 270
Thr Thr Gly Arg Gln Ala Gln Cys Thr Ser Tyr Phe Ile Glu Pro
                275                 280                 285
Val Gln Trp Met Glu Ser Ala Leu Leu Gly Val Met Asp Gly Gln
                290                 295                 300
Leu Leu Cys Pro Lys Cys Ser Ala Lys Leu Gly Ser Phe Asn Trp
                305                 310                 315
Tyr Gly Glu Gln Cys Ser Cys Gly Arg Trp Ile Thr Pro Ala Phe
                320                 325                 330
Gln Ile His Lys Asn Arg Val Asp Glu Met Lys Ile Leu Pro Val
                335                 340                 345
Leu Gly Ser Gln Thr Gly Lys Ile
                350

(2) INFORMATION FOR SEQ ID NO:     4:

(i) SEQUENCE CHARACTERISTICS:
        (A) LENGTH: 207 amino acids
        (B) TYPE: amino acid
        (C) STRANDEDNESS: single
        (D) TOPOLOGY: linear (vii) IMMEDIATE SOURCE:
        (A) LIBRARY: MUSCNOT02
        (B) CLONE: 971204

(xi) SEQUENCE DESCRIPTION: SEQ ID NO: 4 :

Met Cys Pro Gly Asn Trp Leu Trp Ala Ser Met Thr Phe Met Ala
                  5                  10                  15
Arg Phe Ser Arg Ser Ser Arg Ser Pro Val Arg Thr Arg Gly
                 20                  25                  30
Thr Leu Glu Glu Met Pro Thr Val Gln His Pro Phe Leu Asn Val
                 35                  40                  45
Phe Glu Leu Glu Arg Leu Leu Tyr Thr Gly Lys Thr Ala Cys Asn
                 50                  55                  60
His Ala Asp Glu Val Trp Pro Gly Leu Tyr Leu Gly Asp Gln Asp
                 65                  70                  75
Met Ala Asn Asn Arg Arg Glu Leu Arg Arg Leu Gly Ile Thr His
                 80                  85                  90
Val Leu Asn Ala Ser His Ser Arg Trp Arg Gly Thr Pro Glu Ala
                 95                 100                 105
Tyr Glu Gly Leu Gly Ile Arg Tyr Leu Gly Val Pro Ala Phe
                110                 115                 120
Asp Met Ser Ile His Phe Gln Thr Ala Ala Asp Phe Ile His Arg
                125                 130                 135
Ala Leu Ser Gln Pro Gly Gly Lys Ile Leu Val His Cys Ala Val
                140                 145                 150
Gly Val Ser Arg Ser Ala Thr Leu Val Leu Ala Tyr Leu Met Leu
                155                 160                 165
Tyr His His Leu Thr Leu Val Glu Ala Ile Lys Lys Val Lys Asp
                170                 175                 180
His Arg Gly Ile Ile Pro Asn Arg Gly Phe Leu Arg Gln Leu Leu
                185                 190                 195
Ala Leu Asp Arg Arg Leu Arg Gln Gly Leu Glu Ala
                200                 205

(2) INFORMATION FOR SEQ ID NO:     5:
```

(i) SEQUENCE CHARACTERISTICS:
    (A) LENGTH: 453 amino acids
    (B) TYPE: amino acid
    (C) STRANDEDNESS: single
    (D) TOPOLOGY: linear (vii) IMMEDIATE SOURCE:
    (A) LIBRARY: LUNGNOT10
    (B) CLONE: 1376382

(xi) SEQUENCE DESCRIPTION: SEQ ID NO: 5 :

```
Met Ala Leu Val Arg Ala Leu Val Cys Cys Leu Leu Thr Ala Trp
                 5                  10                  15

His Cys Arg Ser Gly Leu Gly Leu Pro Val Ala Pro Ala Gly Gly
                20                  25                  30

Arg Asn Pro Pro Ala Ile Gly Gln Phe Trp His Val Thr Asp
                35                  40                  45

Leu His Leu Asp Pro Thr Tyr His Ile Thr Asp His Thr Lys
                50                  55                  60

Val Cys Ala Ser Ser Lys Gly Ala Asn Ala Ser Asn Pro Gly Pro
                65                  70                  75

Phe Gly Asp Val Leu Cys Asp Ser Pro Tyr Gln Leu Ile Leu Ser
                80                  85                  90

Ala Phe Asp Phe Ile Lys Asn Ser Gly Gln Glu Ala Ser Phe Met
                95                 100                 105

Ile Trp Thr Gly Asp Ser Pro His Val Pro Val Pro Glu Leu
               110                 115                 120

Ser Thr Asp Thr Val Ile Asn Val Ile Thr Asn Met Thr Thr Thr
               125                 130                 135

Ile Gln Ser Leu Phe Pro Asn Leu Gln Val Phe Pro Ala Leu Gly
               140                 145                 150

Asn His Asp Tyr Trp Pro Gln Asp Gln Leu Pro Val Val Thr Ser
               155                 160                 165

Lys Val Tyr Asn Ala Val Ala Asn Leu Trp Lys Pro Trp Leu Asp
               170                 175                 180

Glu Glu Ala Ile Ser Thr Leu Arg Lys Gly Gly Phe Tyr Ser Gln
               185                 190                 195

Lys Val Thr Thr Asn Pro Asn Leu Arg Ile Ile Ser Leu Asn Thr
               200                 205                 210

Asn Leu Tyr Tyr Gly Pro Asn Ile Met Thr Leu Asn Lys Thr Asp
               215                 220                 225

Pro Ala Asn Gln Phe Glu Trp Leu Glu Ser Thr Leu Asn Asn Ser
               230                 235                 240

Gln Gln Asn Lys Glu Lys Val Tyr Ile Ile Ala His Val Pro Val
               245                 250                 255

Gly Tyr Leu Pro Ser Ser Gln Asn Ile Thr Ala Met Arg Glu Tyr
               260                 265                 270

Tyr Asn Glu Lys Leu Ile Asp Ile Phe Gln Lys Tyr Ser Asp Val
               275                 280                 285

Ile Ala Gly Gln Phe Tyr Gly His Thr His Arg Asp Ser Ile Met
               290                 295                 300

Val Leu Ser Asp Lys Lys Gly Ser Pro Val Asn Ser Leu Phe Val
               305                 310                 315

Ala Pro Ala Val Thr Pro Val Lys Ser Val Leu Glu Lys Gln Thr
               320                 325                 330
```

-continued

```
Asn Asn Pro Gly Ile Arg Leu Phe Gln Tyr Asp Pro Arg Asp Tyr
            335                 340                 345

Lys Leu Leu Asp Met Leu Gln Tyr Tyr Leu Asn Leu Thr Glu Ala
            350                 355                 360

Asn Leu Lys Gly Glu Ser Ile Trp Lys Leu Glu Tyr Ile Leu Thr
            365                 370                 375

Gln Thr Tyr Asp Ile Glu Asp Leu Gln Pro Glu Ser Leu Tyr Gly
            380                 385                 390

Leu Ala Lys Gln Phe Thr Ile Leu Asp Ser Lys Gln Phe Ile Lys
            395                 400                 405

Tyr Tyr Asn Tyr Phe Phe Val Ser Tyr Asp Ser Ser Val Thr Cys
            410                 415                 420

Asp Lys Thr Cys Lys Ala Phe Gln Ile Cys Ala Ile Met Asn Leu
            425                 430                 435

Asp Asn Ile Ser Tyr Ala Asp Cys Leu Lys Gln Leu Tyr Ile Lys
            440                 445                 450

His Asn Tyr
```

(2) INFORMATION FOR SEQ ID NO:    6:

(i) SEQUENCE CHARACTERISTICS:
        (A) LENGTH: 270 amino acids
        (B) TYPE: amino acid
        (C) STRANDEDNESS: single
        (D) TOPOLOGY: linear (vii) IMMEDIATE SOURCE:
        (A) LIBRARY: TESTNOT03
        (B) CLONE: 2011230

(xi) SEQUENCE DESCRIPTION: SEQ ID NO: 6 :

```
Met Ala Pro Trp Gly Lys Arg Leu Ala Gly Val Arg Gly Val Leu
             5                  10                  15

Leu Asp Ile Ser Gly Val Leu Tyr Asp Ser Gly Ala Gly Gly Gly
            20                  25                  30

Thr Ala Ile Ala Gly Ser Val Glu Ala Val Ala Arg Leu Lys Arg
            35                  40                  45

Ser Arg Leu Lys Val Arg Phe Cys Thr Asn Glu Ser Gln Lys Ser
            50                  55                  60

Arg Ala Glu Leu Val Gly Gln Leu Gln Arg Leu Gly Phe Asp Ile
            65                  70                  75

Ser Glu Gln Glu Val Thr Ala Pro Ala Pro Ala Ala Cys Gln Ile
            80                  85                  90

Leu Lys Glu Gln Gly Leu Arg Pro Tyr Leu Leu Ile His Asp Gly
            95                 100                 105

Val Arg Ser Glu Phe Asp Gln Ile Asp Thr Ser Asn Pro Asn Cys
           110                 115                 120

Val Val Ile Ala Asp Ala Gly Glu Ser Phe Ser Tyr Gln Asn Met
           125                 130                 135

Asn Asn Ala Phe Gln Val Leu Met Glu Leu Glu Lys Pro Val Leu
           140                 145                 150

Ile Ser Leu Gly Lys Gly Arg Tyr Tyr Lys Glu Thr Ser Gly Leu
           155                 160                 165

Met Leu Asp Val Gly Pro Tyr Met Lys Ala Leu Glu Tyr Ala Cys
           170                 175                 180

Gly Ile Lys Ala Glu Val Val Gly Lys Pro Ser Pro Glu Phe Phe
           185                 190                 195
```

```
Lys Ser Ala Leu Gln Ala Ile Gly Val Glu Ala His Gln Ala Val
            200                 205                 210

Met Ile Gly Asp Asp Ile Val Gly Asp Val Gly Gly Ala Gln Arg
            215                 220                 225

Cys Gly Met Arg Ala Leu Gln Val Arg Thr Gly Lys Phe Arg Pro
            230                 235                 240

Ser Asp Glu His His Pro Glu Val Lys Ala Asp Gly Tyr Val Asp
            245                 250                 255

Asn Leu Ala Glu Ala Val Asp Leu Leu Leu Gln His Ala Asp Lys
            260                 265                 270

(2) INFORMATION FOR SEQ ID NO:      7:

(i) SEQUENCE CHARACTERISTICS:
        (A) LENGTH: 231 amino acids
        (B) TYPE: amino acid
        (C) STRANDEDNESS: single
        (D) TOPOLOGY: linear (vii) IMMEDIATE SOURCE:
        (A) LIBRARY: COLANOT02
        (B) CLONE: 2768301

(xi) SEQUENCE DESCRIPTION: SEQ ID NO: 7 :

Met Cys Gly Asn Thr Met Ser Val Pro Leu Leu Thr Asp Ala Ala
              5                  10                  15

Thr Val Ser Gly Ala Glu Arg Glu Thr Ala Ala Val Ile Phe Leu
             20                  25                  30

His Gly Leu Gly Asp Thr Gly His Ser Trp Ala Asp Ala Leu Ser
             35                  40                  45

Thr Ile Arg Leu Pro His Val Lys Tyr Ile Cys Pro His Ala Pro
             50                  55                  60

Arg Ile Pro Val Thr Leu Asn Met Lys Met Val Met Pro Ser Trp
             65                  70                  75

Phe Asp Leu Met Gly Leu Ser Pro Asp Ala Pro Glu Asp Glu Ala
             80                  85                  90

Gly Ile Lys Lys Ala Ala Glu Asn Ile Lys Ala Leu Ile Glu His
             95                 100                 105

Glu Met Lys Asn Gly Ile Pro Ala Asn Arg Ile Val Leu Gly Gly
            110                 115                 120

Phe Ser Gln Gly Gly Ala Leu Ser Leu Tyr Thr Ala Leu Thr Cys
            125                 130                 135

Pro His Pro Leu Ala Gly Ile Val Ala Leu Ser Cys Trp Leu Pro
            140                 145                 150

Leu His Arg Ala Phe Pro Gln Ala Ala Asn Gly Ser Ala Lys Asp
            155                 160                 165

Leu Ala Ile Leu Gln Cys His Gly Glu Leu Asp Pro Met Val Pro
            170                 175                 180

Val Arg Phe Gly Ala Leu Thr Ala Glu Lys Leu Arg Ser Val Val
            185                 190                 195

Thr Pro Ala Arg Val Gln Phe Lys Thr Tyr Pro Gly Val Met His
            200                 205                 210

Ser Ser Cys Pro Gln Glu Met Ala Ala Val Lys Glu Phe Leu Glu
            215                 220                 225

Lys Leu Leu Pro Pro Val
            230
```

(2) INFORMATION FOR SEQ ID NO: 8:

(i) SEQUENCE CHARACTERISTICS:
        (A) LENGTH: 254 amino acids
        (B) TYPE: amino acid
        (C) STRANDEDNESS: single
        (D) TOPOLOGY: linear (vii) IMMEDIATE SOURCE:
        (A) LIBRARY: SINJNOT02
        (B) CLONE: 2886583

(xi) SEQUENCE DESCRIPTION: SEQ ID NO: 8 :

```
Met Ala Glu Ala Val Leu Arg Val Ala Arg Arg Gln Leu Ser Gln
              5                  10                  15

Arg Gly Gly Ser Gly Ala Pro Ile Leu Leu Arg Gln Met Phe Glu
             20                  25                  30

Pro Val Ser Cys Thr Phe Thr Tyr Leu Leu Gly Asp Arg Glu Ser
             35                  40                  45

Arg Glu Ala Val Leu Ile Asp Pro Val Leu Glu Thr Ala Pro Arg
             50                  55                  60

Asp Ala Gln Leu Ile Lys Glu Leu Gly Leu Arg Leu Leu Tyr Ala
             65                  70                  75

Val Asn Thr His Cys His Ala Asp His Ile Thr Gly Ser Gly Leu
             80                  85                  90

Leu Arg Ser Leu Leu Pro Gly Cys Gln Ser Val Ile Ser Arg Leu
             95                 100                 105

Ser Gly Ala Gln Ala Asp Leu His Ile Glu Asp Gly Asp Ser Ile
            110                 115                 120

Arg Phe Gly Arg Phe Ala Leu Glu Thr Arg Ala Ser Pro Gly His
            125                 130                 135

Thr Pro Gly Cys Val Thr Phe Val Leu Asn Asp His Ser Met Ala
            140                 145                 150

Phe Thr Gly Asp Ala Leu Leu Ile Arg Gly Cys Gly Arg Thr Asp
            155                 160                 165

Phe Gln Gln Gly Cys Ala Lys Thr Leu Tyr His Ser Val His Glu
            170                 175                 180

Lys Ile Phe Thr Leu Pro Gly Asp Cys Leu Ile Tyr Pro Ala His
            185                 190                 195

Asp Tyr His Gly Phe Thr Val Ser Thr Val Glu Glu Glu Arg Thr
            200                 205                 210

Leu Asn Pro Arg Leu Thr Leu Ser Cys Glu Glu Phe Val Lys Ile
            215                 220                 225

Met Gly Asn Leu Asn Leu Pro Lys Pro Gln Gln Ile Asp Phe Ala
            230                 235                 240

Val Pro Ala Asn Met Arg Cys Gly Val Gln Thr Pro Thr Ala
            245                 250
```

(2) INFORMATION FOR SEQ ID NO: 9:

(i) SEQUENCE CHARACTERISTICS:
        (A) LENGTH: 2162 base pairs
        (B) TYPE: nucleic acid
        (C) STRANDEDNESS: single
        (D) TOPOLOGY: linear (vii) IMMEDIATE SOURCE:
        (A) LIBRARY: PITUNOT01
        (B) CLONE: 094168

(xi) SEQUENCE DESCRIPTION: SEQ ID NO: 9 :

```
GTCGGGCAGC AGCGGGGCTG TCTATCCCGG CTGAGGACCC GCGGCCAGTG CGGGTGGCTG      60

GCTTTGCCAT TAGCGGGGGC CTTTCCTGAG GACGGCGTAC GGAGTGTGGG GAATGAAGGA     120

TGGCAGCATG CCGTGCATTA AAAGCTGTTT TGGTAGATCT CAGTGGCACA CTTCACATTG     180

AAGATGCAGC TGTGCCAGGC GCACAGGAAG CTCTTAAAAG GTTACGTGGT GCTTCTGTAA     240

TCATTAGGTT TGTGACCAAT ACAACCAAAG AGAGCAAGCA AGACCTGTTA GAAAGGTTGA     300

GAAAATTGGA ATTTGATATC TCTGAAGATG AAATATTCAC ATCTCTGACT GCAGCCAGAA     360

GTTTACTAGA GCGGAAACAA GTCAGACCCA TGCTGCTAGT TGATGATCGG GCACTACCTG     420

ATTTCAAAGG AATACAAACA AGTGATCCTA ATGCTGTGGT CATGGGATTG GCACCAGAAC     480

ATTTTCATTA TCAAATTCTG AATCAAGCAT TCCGGTTACT CCTGGATGGA GCACCTCTGA     540

TAGCAATCCA CAAAGCCAGG TATTACAAGA GGAAAGATGG CTTAGCCCTG GGGCCTGGAC     600

CATTTGTGAC TGCTTTAGAG TATGCCACAG ATACCAAAGC CACAGTCGTG GGGAAACCAG     660

AGAAGACGTT CTTTTTGGAA GCATTGCGGG GCACTGGCTG TGAACCTGAG GAGGCTGTCA     720

TGATAGGAGA TGATTGCAGG GATGATGTTG GTGGGGCTCA AGATGTCGGC ATGCTGGGCA     780

TCTTAGTAAA GACTGGGAAA TATCGAGCAT CAGATGAAGA AAAAATTAAT CCACCTCCTT     840

ACTTAACTTG TGAGAGTTTC CCTCATGCTG TGGACCACAT TCTGCAGCAC CTATTGTGAA     900

GCAATGTGTG CATCTGAAGC AACTTGAAAT GCAGCTTCTT ATTGTCTGGA ATGAATCCCT     960

TACCAACTCA GTGCCAGCAT CGGTAGACAC CAGTCAGTGC TGATCGCTTT TTAACCCTCT    1020

TTTGTTGTGC ATTAATTAGA AAGAAAGGTA TTGAATTGCG GCTAGCCAGT AAGCCTTGCT    1080

AATCTCTTTT ATTTTGTAAC TGAAGATGAG ACCCAAAGAA AGGGAAAGCT GAGATTTTGT    1140

GCCATTCCTT TTAAAATATT CATCAGGTTA GGTGGGGCTG TGGGGGAAAA GCTACCACAG    1200

GGAAGAGTGT TCTCTGCTGT CTCTTCACTG GAAAACAGGG AGGGGGGATT TCAGACTGTG    1260

AAGAAAGTTG AATGGTGGTT TTTAAATTAT AAAGTAATGT ATTAAAAGGT GCATTAGGCT    1320

GTAGTTCTAA TATTGAGTTC AACTGTGAAA TCCATCAGAT GTGCCAAATG GAGAAGACAG    1380

AAAGCAACAA AGTGAATTGT TCTTTAGCCC AAGTGGTACA GTGAATTTGC TTTAACAGAT    1440

GTTGAAAACT AAATTTTCTA CTGTATTCCC AGCACGGGTG ACTTCTTTTT CTCTTCATTA    1500

GCCAGAGATG ACTAATTTAA ATTTAGAACC AGATTTTAAT TTAAATTAAT ATTTCCATTA    1560

ATAACCTATT CATTGCAGAT ACCTATTATA CTGTGTAACA GTTGTTTTGG AAATTTTATG    1620

TAAAATTAAA ACTATCAGTA TTTTACAGAT GTTTTAATTA GACATTGTTA TTAACAGGAA    1680

CAGTGCAGAA ACTAGAATCA AGCCTTATAA TATCTTATAG ACCATGCATT TTTGAAGTTA    1740

GTGTCCACTA GGGTCCTATT AACTGTACAT TTGCAAGATT TCATTATTTT TGCCTCTGAC    1800

ACTATGGAA AAATTTTTA GAAGCTATTG GGACAGATTC AAGCTTTTAT GCACTTGGTT    1860

ACTACAGCTG TAAAATGAAA TCTCGTCTTG TAGCATGGAT TATTCTTCTC ATGTTAAACC    1920

CACCAAAATA AAGGGGACTA AATAGGTAAT GATTTTCCTA GTGCATTTGC ATACTGTGAT    1980

AATCCTGGGC CTTGCAATAG TTCTACAGGG CTCTTGGGCA TTGAATTATT AGGATGTAAT    2040

TGTACATCAT TGTAGTGTTC ACCTTATTGA AGCTCACTCT GATGTTAATG AGCTTCGGGT    2100

TTTGATGCTT GTTTAGAGAT CAGCAGTCTT GGATGGGAGG GAACAAAGCT AAATAAATGT    2160

TA                                                                    2162
```

(2) INFORMATION FOR SEQ ID NO:    10:

(i) SEQUENCE CHARACTERISTICS:
            (A) LENGTH: 1403 base pairs
            (B) TYPE: nucleic acid
            (C) STRANDEDNESS: single
            (D) TOPOLOGY: linear (vii) IMMEDIATE SOURCE:
            (A) LIBRARY: KIDNNOT02
            (B) CLONE: 195647

(xi) SEQUENCE DESCRIPTION: SEQ ID NO: 10 :

```
CGGGGTGTGG AGCCCGGCCG CTGCTCGCGG GCTGAGTGTC TGTCGCTGCT GCCGCCTCCA    60

CCCAGCCTCC GCCATGGACC TCTTCGGGGA CCTGCCGGAG CCCGAGCGCT CGCCGCGCCC   120

GGCTGCCGGG AAAGAAGCTC AGAAAGGACC CCTGCTCTTT GATGACCTCC CTCCGGCCAG   180

CAGTACTGAC TCAGGATCAG GGGGACCTTT GCTTTTTGAT GATCTCCCAC CCGCTAGCAG   240

TGGCGATTCA GGTTCTCTTG CCACATCAAT ATCCCAGATG GTAAAGACTG AAGGGAAAGG   300

AGCAAAGAGA AAAACCTCCG AGGAAGAGAA GAATGGCAGT GAAGAGCTTG TGGAAAAGAA   360

AGTTTGTAAA GCCTCTTCGG TGATCTTTGG TCTGAAGGGC TATGTGGCTG AGCGGAAGGG   420

TGAGAGGGAG GAGATGCAGG ATGCCCACGT CATCCTGAAC GACATCACCG AGGAGTGTAG   480

GCCCCCATCG TCCCTCATTA CTCGGGTTTC ATATTTTGCT GTTTTTGATG GACATGGAGG   540

AATTCGAGCC TCAAAATTTG CTGCACAGAA TTTGCATCAA AACTTAATCA GAAAATTTCC   600

TAAAGGAGAT GTAATCAGTG TAGAGAAAAC CGTGAAGAGA TGCCTTTTGG ACACTTTCAA   660

GCATACTGAT GAAGAGTTCC TTAAACAAGC TTCCAGCCAG AAGCCTGCCT GGAAAGATGG   720

GTCCACTGCC ACGTGTGTTC TGGCTGTAGA CAACATTCTT TATATTGCCA ACCTCGGAGA   780

TAGTCGGGCA ATCTTGTGTC GTTATAATGA GGAGAGTCAA AAACATGCAG CCTTAAGCCT   840

CAGCAAAGAG CATAATCCAA CTCAGTATGA AGAGCGGATG AGGATACAGA AGGCTGGAGG   900

AAACGTCAGG GATGGGCGTG TTTTGGGCGT GCTAGAGGTG TCACGCTCCA TTGGGGACGG   960

GCAGTACAAG CGCTGCGGTG TCACCTCTGT GCCCGACATC AGACGCTGCC AGCTGACCCC  1020

CAATGACAGG TTCATTTTGT TGGCCTGTGA TGGGCTCTTC AAGGTCTTTA CCCCAGAAGA  1080

AGCCGTGAAC TTCATCTTGT CCTGTCTCGA GGATGAAAAG ATCCAGACCC GGGAAGGGAA  1140

GTCCGCAGCC GACGCCCGCT ACGAAGCAGC CTGCAACAGG CTGGCCAACA AGGCGGTGCA  1200

GCGGGGCTCG GCCGACAACG TCACTGTGAT GGTGGTGCGG ATAGGGCACT GAGGGGTGGC  1260

GCGCGGCCAG GAGCACGCAT GGTATTGACT TAAAAGGTTC ATTTTGTGTG TGTGCACATT  1320

GTGTGTTTTG TGTACTCCTG TGGGACTCCC ATGGTTGTAA ATAAAGGTTT CTCTTTTTTT  1380

TTCCTAAAAA AAAAAAAAAA AAA                                         1403
```

(2) INFORMATION FOR SEQ ID NO:   11:

(i) SEQUENCE CHARACTERISTICS:
            (A) LENGTH: 1358 base pairs
            (B) TYPE: nucleic acid
            (C) STRANDEDNESS: single
            (D) TOPOLOGY: linear (vii) IMMEDIATE SOURCE:
            (A) LIBRARY: TMLR3DT02
            (B) CLONE: 507537

(xi) SEQUENCE DESCRIPTION: SEQ ID NO: 11 :

```
GTACCACGCG TCCGAGAGCC GCCGAGGCTG GCGAGTCCCA GGGGAAGGAT GTTCTAGCCG    60

GAGTCTACTC GATGGTAGGG CAGGAAGCCG CCTTGTCTCT GGGCGCGGCC ATGTTGGAGG   120
```

```
CTCCGGGCCC GAGTGATGGC TGCGAGCTCA GCAACCCCAG CGCCAGCAGA GTCAGCTGTG      180

CCGGGCAGAT GCTGGAAGTG CAGCCAGGAT TGTATTTCGG TGGGGCCGCG GCCGTCGCGG      240

AGCCAGATCA CCTGAGGGAA GCGGGCATCA CGGCCGTGCT AACAGTGGAC TCGGAGGAGC      300

CCAGCTTCAA GGCGGGGCCT GGGGTCGAGG ATCTATGGCG CCTCTTCGTG CCAGCGCTGG      360

ACAAACCCGA GACGGACCTA CTCAGCCATC TGGACCGGTG CGTGGCCTTC ATCGGTCAGG      420

CCCGCGCTGA GGGCCGTGCG GTGTTGGTGC ACTGTCATGC AGGAGTCAGT CGAAGTGTGG      480

CCATAATAAC TGCTTTTCTC ATGAAGACTG ACCAACTTCC CTTTGAAAAA GCCTATGAAA      540

AGCTCCAGAT TCTCAAACCA GAGGCTAAGA TGAATGAGGG GTTTGAGTGG CAACTGAAAT      600

TATACCAGGC AATGGGATAC GAAGTGGATA CCTCTAGTGC AATTTATAAG CAATATCGTT      660

TACAAAAGGT TACAGAGAAG TATCCAGAAT TGCAGAATTT ACCTCAAGAA CTCTTTGCTG      720

TTGACCCAAC TACCGTTTCA CAAGGATTGA AAGATGAGGT TCTCTACAAG TGTAGAAAGT      780

GCAGGCGATC ATTATTTCGA AGTTCTAGTA TTCTGGATCA CCGTGAAGGA AGTGGACCTA      840

TAGCCTTTGC CCACAAGAGA ATGACACCAT CTTCCATGCT TACCACAGGG AGGCAAGCTC      900

AATGTACATC TTATTTCATT GAACCTGTAC AGTGGATGGA ATCTGCTTTG TTGGGAGTGA      960

TGGATGGACA GCTTCTTTGC CCAAAATGCA GTGCCAAGTT GGGTTCCTTC AACTGGTATG     1020

GTGAACAGTG CTCTTGTGGT AGGTGGATAA CACCTGCTTT TCAAATACAT AAGAATAGAG     1080

TGGATGAAAT GAAAATATTG CCTGTTTTGG GATCACAAAC AGGAAAAATA TGAACATGAT     1140

ATTTTATAGC TTGGGAAGAA ACTTGCAGAT GATATGTGCT GCCTTTGCTT CTTATCATTC     1200

ATGGCAGATT GTTTGTGCTT TCAACATTTC ATTTGAAATG GGAGAAGATA AAATCACTTG     1260

ATGTAACCTG GAAACTATGC TTTACATGGC AATCAAAGCC TTTTGATCAT GTACATTTTA     1320

TTTGATATTA AATCTTTTA TAACCAGAAA AAAAAAA                              1358
```

(2) INFORMATION FOR SEQ ID NO: 12:

(i) SEQUENCE CHARACTERISTICS:
        (A) LENGTH: 1691 base pairs
        (B) TYPE: nucleic acid
        (C) STRANDEDNESS: single
        (D) TOPOLOGY: linear (vii) IMMEDIATE SOURCE:
        (A) LIBRARY: MUSCNOT02
        (B) CLONE: 971204

(xi) SEQUENCE DESCRIPTION: SEQ ID NO: 12 :

```
CACGCATGCA TTCCAGGCGG TGCTGCTGGG GCTCGGCGGG GCCGTGTCTG GTCTGCAAGG       60

CGCGCGGGCT CGTGGGGGGT TGGCTGGGGA GCCCACGCTG CCTGGCGACT CGGGCCACCG      120

AATGTGAGAC CGAGTCCCTT TATGTCACCA GCGCACACGC TGATTTGAAC CCTGCTTCGA      180

CGTGTGTGTC ATGGCTTAAA AATAGCTGCT AATCTGTCAA CCTGTCTTGG GCAGAAACAG      240

CGGCGGCGAC AGCAGCAGGA GCGTCATGGC CGTGGCGCTG TCTGCGCCGG CGATCCGCCT      300

TTCGGACTGA GGCCCAGCGC AGCGCTTGCA AAGAGCAGCA GCTACCTGGC AACTGAACCC      360

ATCATCACCA CAGCCACTCC TGCAGCTGCC ACGGTTTCTG CCACCTCTAA GATGTGCCCT      420

GGTAACTGGC TTTGGGCTTC TATGACTTTT ATGGCTCGCT TCTCCCGGAG TAGCTCAAGG      480

TCTCCTGTTC GAACTCGAGG GACCCTGGAG GAGATGCCAA CCGTTCAACA TCCTTTCCTC      540

AATGTCTTCG AGTTGGAGCG GCTCCTCTAC ACAGGCAAGA CAGCCTGTAA CCATGCCGAC      600

GAGGTCTGGC CAGGCCTCTA TCTCGGAGAC CAGGACATGG CTAACAACCG CCGGGAGCTT      660
```

-continued

| | |
|---|---|
| CGCCGCCTGG GCATCACGCA CGTCCTCAAT GCCTCACACA GCCGGTGGCG AGGCACGCCC | 720 |
| GAGGCCTATG AGGGGCTGGG CATCCGCTAC CTGGGTGTTG AGCCAGCCTT TGACATGAGC | 780 |
| ATCCACTTCC AGACGGCTGC CGACTTCATC CACCGGGCGC TGAGCCAGCC AGGAGGGAAG | 840 |
| ATCCTGGTGC ATTGTGCTGT GGGCGTGAGC CGATCCGCCA CCCTGGTACT GGCCTACCTC | 900 |
| ATGCTGTACC ACCACCTTAC CCTCGTGGAG GCCATCAAGA AAGTCAAAGA CCACCGAGGC | 960 |
| ATCATCCCCA ACCGGGGCTT CCTGAGGCAG CTCCTGGCCC TGGACCGCAG GCTGCGGCAG | 1020 |
| GGTCTGGAAG CATGAGGGGA GGGGGAGAGA GGTCAGGCCA GGCCCGTGGG TAGGTCCCTG | 1080 |
| GCTCCCAGCT GGAGATAGGA GGCCCAGGTG GCAGGTAGCA GGAGGCCCAG ATCACCCATC | 1140 |
| CTCCCCTGGG GTCAGGAGAG GCCGAGCCCC AGGCCACTGT CACTCTTTGC GGGAGGGGAC | 1200 |
| GGGGAGTGAG GTTGGGCAGT GTGGTGGATG GGCACCCAGG AAGGGTTGAC CAGGGAAGGA | 1260 |
| GGCAGCTAGG CTGTAGATGG AAGATGGTCC TGGGATTCGA ACACCGCTGG GATCTGGCTA | 1320 |
| GGGTGCTCCC TGGGATTCAC AGTCCCTTCC CCTCTTTGTG CCCAAGTGTT TCCCTCTCTC | 1380 |
| CCTCACCAAA ACAAAAGGGC CATCTCTGCC CTGCACTTGT GCAGAAAGTC AGGGATACGG | 1440 |
| CAAGCATGAA TGCAATGGTG TAGAGTTGTG TGAAACCCCT AGCATAGAGA CAGACAGCGA | 1500 |
| AGAGATGGTG TGAAAAGCTT GCAGAACCAG ACAGAGAACC CCACAGACTT TCCACTCCAA | 1560 |
| GCACAGGAGG AGGTAGCTAG CGTGTGAGGG TTGGCACTAG GCCCACGGCT GCTGCTTGGG | 1620 |
| CCAAAAACAT ACAGAGGTGC ATGGCTGGCA GTCTTGAAAT TGTCACTCGC TTACTGGATC | 1680 |
| CAAGTGTCTC G | 1691 |

(2) INFORMATION FOR SEQ ID NO: 13:

(i) SEQUENCE CHARACTERISTICS:
        (A) LENGTH: 1764 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT10
        (B) CLONE: 1376382

(xi) SEQUENCE DESCRIPTION: SEQ ID NO: 13 :

| | |
|---|---|
| CTCAGGCCTG ACGGTCCGAG TGGAGCTGCG GGACAGCCCG AACCTCCAGG TCAGCCCCGC | 60 |
| GGCCCTCCAT GGCGCTGGTG CGCGCACTCG TCTGCTGCCT GCTGACTGCC TGGCACTGCC | 120 |
| GCTCCGGCCT CGGGCTGCCC GTGGCGCCCG CAGGCGGCAG GAATCCTCCT CCGGCGATAG | 180 |
| GACAGTTTTG GCATGTGACT GACTTACACT TAGACCCTAC TTACCACATC ACAGATGACC | 240 |
| ACACAAAAGT GTGTGCTTCA TCTAAAGGTG CAAATGCCTC CAACCCTGGC CCTTTTGGAG | 300 |
| ATGTTCTGTG TGATTCTCCA TATCAACTTA TTTTGTCAGC ATTTGATTTT ATTAAAAATT | 360 |
| CTGGACAAGA AGCATCTTTC ATGATATGGA CAGGGGATAG CCCACCTCAT GTTCCTGTAC | 420 |
| CTGAACTCTC AACAGACACT GTTATAAATG TGATCACTAA TATGACAACC ACCATCCAGA | 480 |
| GTCTCTTTCC AAATCTCCAG GTTTTCCCTG CGCTGGGTAA TCATGACTAT TGGCCACAGG | 540 |
| ATCAACTGCC TGTAGTCACC AGTAAAGTGT ACAATGCAGT AGCAAACCTC TGGAAACCAT | 600 |
| GGCTAGATGA AGAAGCTATT AGTACTTTAA GGAAGGTGG TTTTTATTCA CAGAAAGTTA | 660 |
| CAACTAATCC AAACCTTAGG ATCATCAGTC TAAACACAAA CTTGTACTAC GGCCCAAATA | 720 |
| TAATGACACT GAACAAGACT GACCCAGCCA ACCAGTTTGA ATGGCTAGAA AGTACATTGA | 780 |
| ACAACTCTCA GCAGAATAAG GAGAAGGTGT ATATCATAGC ACATGTTCCA GTGGGGTATC | 840 |

-continued

```
TGCCATCTTC ACAGAACATC ACAGCAATGA GAGAATACTA TAATGAGAAA TTGATAGATA    900

TTTTTCAAAA ATACAGTGAT GTCATTGCAG GACAATTTTA TGGACACACT CACAGAGACA    960

GCATTATGGT TCTTTCAGAT AAAAAAGGAA GTCCAGTAAA TTCTTTGTTT GTGGCTCCTG   1020

CTGTTACACC AGTGAAGAGT GTTTTAGAAA AACAGACCAA CAATCCTGGT ATCAGACTGT   1080

TTCAGTATGA TCCTCGTGAT TATAAATTAT TGGATATGTT GCAGTATTAC TTGAATCTGA   1140

CAGAGGCGAA TCTAAAGGGA GAGTCCATCT GGAAGCTGGA GTATATCCTG ACCCAGACCT   1200

ACGACATTGA AGATTTGCAG CCGGAAAGTT TATATGGATT AGCTAAACAA TTTACAATCC   1260

TAGACAGTAA GCAGTTTATA AAATACTACA ATTACTTCTT TGTGAGTTAT GACAGCAGTG   1320

TAACATGTGA TAAGACATGT AAGGCCTTTC AGATTTGTGC AATTATGAAT CTTGATAATA   1380

TTTCCTATGC AGATTGCCTC AAACAGCTTT ATATAAAGCA CAATTACTAG TATTTCACAG   1440

TTTTTGCTAA TAGAAAATGC TGATTCTGAT TCTGAGATCA ATTTGTGGGA ATTTTACATA   1500

AATCTTTGTT AATTACTGAG TGGGCAAGTA GACTTCCTGT CTTTGCTTTC TTTTTTTTTT   1560

TCTTTTTGAT GCCTTAATGT AGATATCTTT ATCATTCTGA ATTGTATTAT ATATTTAAAG   1620

TGCTCATTAA TAGAATGATG GATGTAAATT GGATGTAAAT ATTCAGTTTA TATAATTATA   1680

TCTAATTTGT ACCCTTGTTG AAATTGTCAT TTATACAATA AAGCGAATTC TTTATCTCTA   1740

AATATGAAAA AAAAAAAAA AAGG                                          1764
```

(2) INFORMATION FOR SEQ ID NO: 14:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear (vii) IMMEDIATE SOURCE:
        (A) LIBRARY: TESTNOT03
        (B) CLONE: 2011230

(xi) SEQUENCE DESCRIPTION: SEQ ID NO: 14 :

```
GGAGCAGGGC CGGGCGCCAT GGCACCGTGG GGCAAGCGGC TGGCTGGCGT GCGCGGGGTG     60

CTGCTTGACA TCTCGGGCGT GCTGTACGAC AGCGGCGCGG GCGGCGGCAC GGCCATCGCC    120

GGCTCGGTGG AGGCGGTGGC CAGACTGAAG CGTTCCCGGC TGAAGGTGAG GTTCTGCACC    180

AACGAGTCGC AGAAGTCCCG GGCAGAGCTG GTGGGGCAGC TTCAGAGGCT GGGATTTGAC    240

ATCTCTGAGC AGGAGGTGAC CGCCCCGGCA CCAGCTGCCT GCCAGATCCT GAAGGAGCAA    300

GGCCTGCGAC CATACCTGCT CATCCATGAC GGAGTCCGCT CAGAATTTGA TCAGATCGAC    360

ACATCCAACC CAAACTGTGT GGTAATTGCA GACGCAGGAG AAAGCTTTTC TTATCAAAAC    420

ATGAATAACG CCTTCCAGGT GCTCATGGAG CTGGAAAAAC CTGTGCTCAT ATCACTGGGA    480

AAAGGGCGTT ACTACAAGGA GACCTCTGGC CTGATGCTGG ACGTTGGTCC CTACATGAAG    540

GCGCTTGAGT ATGCCTGTGG CATCAAAGCC GAGGTGGTGG GGAAGCCTTC TCCTGAGTTT    600

TTCAAGTCTG CCCTGCAAGC GATAGGAGTG GAAGCCCACC AGGCCGTCAT GATTGGGGAC    660

GATATCGTGG GCGACGTCGG CGGTGCCCAG CGGTGTGGAA TGAGAGCGCT GCAGGTGCGC    720

ACCGGGAAGT TCAGGCCCAG TGACGAGCAC CATCCGGAAG TGAAGGCTGA TGGGTACGTG    780

GACAACCTCG CAGAGGCAGT GGACCTGCTG CTGCAGCACG CCGACAAGTG ATGGCCTCCT    840

GGGAGAACCC CGCCTCCTCC ACCCCTGCCT CTCCTCACCC CCTGCCTCCC CTCCACCCCT    900

GCCTCTTCTC CACCCGCCCA GGAGAGCCCC ACCTCCTCCA CCCCTGCCTC TCCTCCACCC    960
```

-continued

| | |
|---|---|
| CTGCCTCCCC TCCACCTGCC CCAGTGCCCA GACCAACCAA GGCCCTGACA GCCCTGCCTT | 1020 |
| CTGCCCTCTG CCCTGCATGG GCAGGCATTT GTTCCCTACC TGGGTGGCCT GCTCCCCTGC | 1080 |
| CTGGGCCCTG ACTTCAGCTC CCTGTAGTGA AGTCCAGGAG GGTGGGACAG GCCTGTCAGG | 1140 |
| CCTCTGGGAA TCTCCCAAAT CCCAGAACTC ACCACTCACC ATGGGCCTTT AAATGCAGTA | 1200 |
| AACTCCACCT AACCAGATTC AGGGGCACTA TGCCCACTGC CTCCTCTTCA GACTCTTTGC | 1260 |
| ATTTCAGTGA AGAGCCTGGA AGAAACCCAG GGGCCTCCTA TGCACAGATC TTGCAGCCCA | 1320 |
| GAACCAAGTC AGCCTCCCTG CGACTGCCCA GGCACACTGC CCACCACCCC ACCCCCGAAA | 1380 |
| CAATGCCAGC CCGCTGCTTT TTCTATCCTC CCAGTCACCT TTGCAGACAA AGACCAGGGG | 1440 |
| CAGCTCCCGA GGGCACTGTG AAGGCTCCCA TGCCACACAG TGAGAACTGT AGCCTCTGCG | 1500 |
| TCCAAGGCAC ACAGGGTACT TTCTGGACCC ACTGCTGGAC AGACTTGAAG GTGTCATGCC | 1560 |
| CGGTGTGTGC AGGAGGAAAC TAACAGTTCA GTAAACTCTG CCTTGACCAG CAAAAAAAAA | 1620 |
| A | 1621 |

(2) INFORMATION FOR SEQ ID NO: 15:

(i) SEQUENCE CHARACTERISTICS:
        (A) LENGTH: 1624 base pairs
        (B) TYPE: nucleic acid
        (C) STRANDEDNESS: single
        (D) TOPOLOGY: linear (vii) IMMEDIATE SOURCE:
        (A) LIBRARY: COLANOT02
        (B) CLONE: 2768301

(xi) SEQUENCE DESCRIPTION: SEQ ID NO: 15 :

| | |
|---|---|
| TGCGGGGCG GCCGAGGGGG AAGAGTGTGT CTGCGGGAGA AAGAGGAGAA TCGCCCAAGC | 60 |
| GGCCTCGGAA GTCCCAGGGA GTGGAGGCCC CCGCCGTGGA GCCGTGTGGT GTATGTGTGG | 120 |
| TAACACCATG TCTGTGCCCC TGCTCACCGA TGCTGCCACC GTGTCTGGAG CTGAGCGGGA | 180 |
| AACGGCCGCG GTTATTTTTT TACATGGACT TGGAGACACA GGGCACAGCT GGGCTGACGC | 240 |
| CCTCTCCACC ATCCGGCTCC CTCACGTCAA GTACATCTGT CCCCATGCGC CTAGGATCCC | 300 |
| TGTGACCCTC AACATGAAGA TGGTGATGCC CTCCTGGTTT GACCTGATGG GGCTGAGTCC | 360 |
| AGATGCCCCA GAGGACGAGG CTGGCATCAA GAAGGCAGCA GAGAACATCA AGGCCTTGAT | 420 |
| TGAGCATGAA ATGAAGAACG GGATCCCTGC CAATCGAATC GTCCTGGGAG GCTTTTCACA | 480 |
| GGGCGGGGCC CTGTCCCTCT ACACGGCCCT CACCTGCCCC CACCCTCTGG CTGGCATCGT | 540 |
| GGCGTTGAGC TGCTGGCTGC CTCTGCACCG GGCCTTCCCC CAGGCAGCTA ATGGCAGTGC | 600 |
| CAAGGACCTG GCCATACTCC AGTGCCATGG GGAGCTGGAC CCCATGGTGC CCGTACGGTT | 660 |
| TGGGGCCCTG ACGGCTGAGA AGCTCCGGTC TGTTGTCACA CCTGCCAGGG TCCAGTTCAA | 720 |
| GACATACCCG GGTGTCATGC ACAGCTCCTG TCCTCAGGAG ATGGCAGCTG TGAAGGAATT | 780 |
| TCTTGAGAAG CTGCTGCCTC CTGTCTAACT AGTCGCTGGC CCAGTGCAG TACCCCAGCT | 840 |
| CATGGGGAC TCAGCAAGCA AGCGTGGCAC CATCTTGGAT CTGAGCCGGT CGAGCCCCTG | 900 |
| TCCCCACCCT TCCTGACCTG TCCTTTTCCC ACAGGCCTCT GGGGGCAGGT GGCAAGGCCT | 960 |
| GGCCGGGCCT TCCTTCCTGG CCTTAGCCAC CTGGCTCTGT CTGCAGCAGG GGCAGGCTGC | 1020 |
| TTTCTTATCC ATTTCCCTGG AGGCGGGCCC CCCTGGCAGC AGTATTGGAG GGGCTACAGG | 1080 |
| CAGCTGGAGA AAGGGGCCCA GCCGCTGACC CACTCACTCA GGACCTCACT CACTAGCCCC | 1140 |
| GCTTTGGGCC CCCTCCTGTG ACCTCAGGGT TTGGCCCATG GGGCCCTCCC AGGCCCCTGC | 1200 |

-continued

```
CCCAACTGAT TCTGCCCAGA TAATCGTGTC TCCTGCCTCC ACTCAGCTGC TTCTCAGTCA    1260

TGAATGTGGC CATGGCCCCG GGGTCCCCTT GCTGCTGTGG GCTCCCTGTC CCTGGGCAGG    1320

AGTGCTGGTG AGGAGGTGGA GCCTTTTGAG GGGGGCCTTC CCTCAGCTGT TTCCCCACAC    1380

TGGGGGGCTG GGCCCTGCCT CCCCGTTACC CTCCTTCCCT GCAGGCCTGG AGCCTGTAGG    1440

GCTGGACTGA GGTTCAGGTC TCCCCCCAGC TGTCTCACCC CCACTTTGTC CCCACTCTAG    1500

AGCAGGGAGG CAGTGGGGGA GGAGTTGTGT CTCGTCTTCT GTCTCCATGT GGTTTTTGGG    1560

TGTTTTTCTT GTTGTGTCCT GGATTCCGAT AAAATTAAAG AAATTGCTTC CTCAAAAAAA    1620

AAAA                                                                 1624

(2) INFORMATION FOR SEQ ID NO:   16:

(i) SEQUENCE CHARACTERISTICS:
         (A) LENGTH: 973 base pairs
         (B) TYPE: nucleic acid
         (C) STRANDEDNESS: single
         (D) TOPOLOGY: linear (vii) IMMEDIATE SOURCE:
         (A) LIBRARY: SINJNOT02
         (B) CLONE: 2886583

(xi) SEQUENCE DESCRIPTION: SEQ ID NO: 16 :

AGCCGTAGCG CCCGGCTCCT GCAGGCGCTC GGCCTCCGCT CATTCCTGAC CCCGCAGTGG      60

GCGCGATGGC GGAGGCTGTA CTGAGGGTCG CCCGGCGGCA GCTGAGCCAG CGCGGCGGGT     120

CTGGAGCCCC CATCCTCCTG CGGCAGATGT TCGAGCCTGT GAGCTGCACC TTCACGTACC     180

TGCTGGGTGA CAGAGAGTCC CGGGAGGCCG TTCTGATCGA CCCAGTCCTG GAAACAGCGC     240

CTCGGGATGC CCAGCTGATC AAGGAGCTGG GGCTGCGGCT GCTCTATGCT GTGAATACCC     300

ACTGCCACGC GGACCACATT ACAGGCTCGG GGCTGCTCCG TTCCCTCCTC CCTGGCTGCC     360

AGTCTGTCAT CTCCCGCCTT AGTGGGGCCC AGGCTGACTT ACACATTGAG GATGGAGACT     420

CCATCCGCTT CGGGCGCTTC GCGTTGGAGA CCAGGGCCAG CCCTGGCCAC ACCCCAGGCT     480

GTGTCACCTT CGTCCTGAAT GACCACAGCA TGGCCTTCAC TGGAGATGCC CTGTTGATCC     540

GTGGGTGTGG GCGGACAGAC TTCCAGCAAG GCTGTGCCAA GACCTTGTAC CACTCGGTCC     600

ATGAAAAGAT CTTCACACTT CCAGGAGACT GTCTGATCTA CCCTGCTCAC GATTACCATG     660

GGTTCACAGT GTCCACCGTG GAGGAGGAGA GGACTCTGAA CCCTCGGCTC ACCCTCAGCT     720

GTGAGGAGTT TGTCAAAATC ATGGGCAACC TGAACTTGCC TAAACCTCAG CAGATAGACT     780

TTGCTGTTCC AGCCAACATG CGCTGTGGGG TGCAGACACC CACTGCCTGA TCTCACTTCT     840

GTCAGATGCT CCCATCCACT ATTAATGCAC TAGGTGGGAG GAGAGGGCGG CAATGACACT     900

GCACCTCTCC TTTCCCACCG CATTCCCTGG AGCTCCCTAA ATAAAACTTT TTTTATCGTG     960

AAAAAAAAAA AAA                                                       973
```

HYDROLASE ENZYMES

FIELD OF THE INVENTION

This invention relates to nucleic acid and amino acid sequences of human hydrolase-like molecules and to the use of these sequences in the diagnosis, treatment, and prevention of cell proliferation disorders, and autoimmune disorders.

BACKGROUND OF THE INVENTION

Hydrolysis is a common enzymatic mechanism. There are numerous enzymes whose catalytic mechanism involves breaking a covalent bond in a substrate by the addition of a molecule of water across the bond. The reaction involves a nucleophilic attack by the water molecule's oxygen atom on a target bond within the substrate and results in a splitting of the water molecule across the target bond, thereby breaking the bond and generating two product molecules. This general mechanism applies to a wide variety of enzymes including phosphatases, lysophospholipases, glyoxalases, and phosphodiesterases.

The protein phosphorylation/dephosphorylation cycle is one of the major regulatory mechanisms employed by eukaryotic cells to control cellular activities. During protein phosphorylation, phosphate groups are transferred from adenosine triphosphate molecules to a protein by protein kinases. During protein dephosphorylation, phosphate groups are removed from a protein by protein phosphatases, using a hydrolytic mechanism. In this manner, phosphatases are involved in the control of many cellular signaling events that regulate cell growth and differentiation, cell-to-cell contact, the cell cycle, and oncogenesis.

Lysophospholipases (LPLs) are widely distributed enzymes that regulate intracellular lipids, and occur in numerous isoforms. These isoforms vary in molecular mass, the substrate metabolized, and the optimum pH required for activity. Small isoforms, approximately 15–30 kD, function as hydrolases; large isoforms, those exceeding 60 kD, function both as hydrolases and transacylases. A particular substrate for LPLs, lysophosphatidylcholine, causes lysis of cell membranes when it is formed or imported into a cell. LPLs are regulated by lipid factors including acylcarnitine, arachidonic acid, and phosphatidic acid. Thus, the activity of LPLs is regulated by signaling molecules important in numerous pathways including the inflammatory response.

The glyoxylase system consists of glyoxylase I, which catalyzes the formation of S-D-lactoylglutathione from methyglyoxal, a side product of triose-phosphate energy metabolism, and glyoxylase II, which hydrolyzes S-D-lactoylglutathione to D-lactic acid and reduced glutathione. Methyglyoxal levels are elevated during hyperglycemia and are likely due to increased triose-phosphate energy metabolism. Elevated levels of glyoxylase II activity have been found in human and in a rat model of non-insulin-dependent diabetes mellitus. The glyoxylase system has been implicated in the detoxification of bacterial toxins and in the control of cell proliferation and microtubule assembly. Elevated levels of S-D-lactoylglutathione, the substrate of glyoxylase II, induced growth arrest and toxicity in HL60 cells. Thus, the glyoxylase system, and glyoxylase II in particular, may be associated with cell proliferation and autoimmune disorders such as diabetes.

Sphingomyelin is a membrane phospholipid that is hydrolyzed to ceramide and phosphatidylcholine by the action of the phosphodiesterase, acid sphingomyelinase. Phosphatidylcholine is involved in numerous intracellular signaling pathways, while ceramide is an essential precursor for the generation of gangliosides, membrane lipids found in high concentration in neural tissue. Defective acid sphingomyelinase phosphodiesterase leads to a build-up of sphingomyelin molecules in lysosomes, resulting in Niemann-Pick disease.

The discovery of new human hydrolase-like molecules and the polynucleotides encoding them satisfies a need in the art by providing new compositions which are useful in the diagnosis, treatment, and prevention of cell proliferation disorder, and autoimmune disorders.

SUMMARY OF THE INVENTION

The invention features substantially purified polypeptides, human hydrolase-like molecules, referred to collectively as "HHLM" and individually as "HHLM-1", "HHLM-2", "HHLM-3", "HHLM-4", "HHLM-5", "HHLM-6", "HHLM-7", and "HHLM-8." In one aspect, the invention provides a substantially purified polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO: 1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8.

The invention further provides a substantially purified variant having at least 90% amino acid identity to the amino acid sequences of SEQ ID NO: 1, SEQ D NO:2, SEQ ID NO:3, SEQ ID NO:4, SEQ ID NO:5, SEQ ID NO:6, SEQ ID NO:7, or SEQ ID NO:8, or a fragment thereof. The invention also provides an isolated and purified polynucleotide encoding the polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO: 1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8. The invention also includes an isolated and purified polynucleotide variant having at least 90% polynucleotide sequence identity to the polynucleotide encoding the polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO: 1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8.

Additionally, the invention provides an isolated and purified polynucleotide which hybridizes under stringent conditions to the polynucleotide encoding the polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8, as well as an isolated and purified polynucleotide having a sequence which is complementary to the polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8.

The invention also provides an isolated and purified polynucleotide comprising a polynucleotide sequence selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, a fragment of SEQ ID NO:9, a fragment of SEQ ID NO:10, a fragment of SEQ ID NO:11, a fragment of SEQ ID NO:12, a fragment of SEQ ID NO:13, a fragment of SEQ ID NO:14, a fragment of SEQ ID NO:15, and a fragment of SEQ ID NO:16. The invention further provides an isolated and purified polynucleotide variant having at least 90% polynucleotide sequence identity to the polynucleotide sequence comprising a polynucleotide sequence selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, a fragment of SEQ ID NO:9, a fragment of SEQ ID NO:10, a fragment of SEQ ID NO:11, a fragment of SEQ ID NO:12, a fragment of SEQ ID NO:13, a fragment of SEQ ID NO:14, a fragment of SEQ ID NO:15, and a fragment of SEQ ID NO:16, as well as an isolated and purified polynucleotide having a sequence which is complementary to the polynucleotide comprising a polynucleotide sequence selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, a fragment of SEQ ID NO:9, a fragment of SEQ ID NO:10, a fragment of SEQ ID NO:11, a fragment of SEQ ID NO:12, a fragment of SEQ ID NO:13, a fragment of SEQ ID NO:14, a fragment of SEQ ID NO:15, and a fragment of SEQ ID NO:16.

The invention further provides an expression vector containing at least a fragment of the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8. In another aspect, the expression vector is contained within a host cell.

The invention also provides a method for producing a polypeptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified HHLM having the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8 in conjunction with a suitable pharmaceutical carrier.

The invention further includes a purified antibody which binds to a polypeptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8, as well as a purified agonist and a purified antagonist to the polypeptide.

The invention also provides a method for treating or preventing a cell proliferation disorder, the method comprising administering to a subject in need of such treatment an effective amount of an antagonist of the polypeptide having an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8.

The invention also provides a method for treating or preventing an autoimmune disorder, the method comprising administering to a subject in need of such treatment an effective amount of an antagonist of the polypeptide having an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8.

The invention also provides a method for detecting a polynucleotide encoding the polypeptide comprising the amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8 in a biological sample containing nucleic acids, the method comprising the steps of: (a) hybridizing the complement of the polynucleotide sequence encoding the polypeptide comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HHLM," as used herein, refers to the amino acid sequences of substantially purified HHLM obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HHLM, increases or prolongs the duration of the effect of HHLM. Agonists may include proteins, nucleic acids, carbohydrates, or any other molecules which bind to and modulate the effect of HHLM.

An "allele" or an "allelic sequence," as these terms are used herein, is an alternative form of the gene encoding HHLM. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HHLM, as described herein, include those sequences with deletions, insertions, or substitutions of different nucleotides, resulting in a polynucleotide the same HHLM or a polypeptide with at least one functional characteristic of HHLM. Included within this definition are polymorphisms which may or may not be readily detectable using a particular oligonucleotide probe of the polynucleotide encoding HHLM, and improper or unexpected hybridization to alleles, with a locus other than the normal chromosomal locus for the polynucleotide sequence encoding HHLM. The encoded protein may also be "altered," and may contain deletions, insertions, or substitutions of amino acid residues which produce a silent change and result in a functionally equivalent HHLM.

Deliberate amino acid substitutions may be made on the basis of similarity in polarity, charge, solubility, hydrophobicity, hydrophilicity, and/or the amphipathic nature of the residues, as long as the biological or immunological activity of HHLM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HHLM which are preferably about 5 to about 15 amino acids in length and which retain some biological activity or immunological activity of HHLM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to HHLM, decreases the amount or the duration of the effect of the biological or immunological activity of HHLM. Antagonists may include proteins, nucleic acids, carbohydrates, antibodies, or any other molecules which decrease the effect of HHLM.

As used herein, the term "antibody" refers to intact molecules as well as to fragments thereof, such as Fa, F(ab')$_2$, and Fv fragments, which are capable of binding the epitopic determinant. Antibodies that bind HHLM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HHLM, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HHLM or fragments of HHLM may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR kit (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HHLM, by northern analysis is indicative of the presence of nucleic acids encoding HHLM in a sample, and thereby correlates with expression of the transcript from the polynucleotide encoding HHLM.

A "deletion," as the term is used herein, refers to a change in the amino acid or nucleotide sequence that results in the absence of one or more amino acid residues or nucleotides.

The term "derivative," as used herein, refers to the chemical modification of HHLM, of a polynucleotide sequence encoding HHLM, or of a polynucleotide sequence complementary to a polynucleotide sequence encoding HHLM. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the Clustal method. (See, e.g., Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat. Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

The term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides or oligonucleotides arrayed on a substrate, e.g., paper, nylon or any other type of membrane, filter, chip, glass slide, or any other suitable solid support.

The term "modulate," as it appears herein, refers to a change in the activity of HHLM. For example, modulation may cause an increase or a decrease in protein activity, binding characteristics, or any other biological, functional, or immunological properties of HHLM.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HHLM, or fragments thereof, or HHLM itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HHLM, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The Invention

The invention is based on the discovery of new human hydrolase-like molecules (HHLM), the polynucleotides encoding HHLM, and the use of these compositions for the diagnosis, treatment, or prevention of cell proliferation disorders, and autoimmune disorders. Table 1 shows the sequence identification numbers, Incyte Clone identification number, and cDNA library for each of the human hydrolase-like molecules disclosed herein.

TABLE 1

| Protein | Nucleotide | Clone ID | Library |
|---------|------------|----------|---------|
| SEQ ID NO:1 | SEQ ID NO:9 | 094168 | PITUNOT1 |
| SEQ ID NO:2 | SEQ ID NO:10 | 195647 | KIDNNOT02 |
| SEQ ID NO:3 | SEQ ID NO:11 | 507537 | TMLR3DT02 |
| SEQ ID NO:4 | SEQ ID NO:12 | 971204 | MUSCNOT02 |
| SEQ ID NO:5 | SEQ ID NO:13 | 1376382 | LUNGNOT10 |
| SEQ ID NO:6 | SEQ ID NO:14 | 2011230 | TESTNOT03 |
| SEQ ID NO:7 | SEQ ID NO:15 | 2768301 | COLANOT02 |
| SEQ ID NO:8 | SEQ ID NO:16 | 2886583 | SINJNOT02 |

Nucleic acids encoding the HHLM-1 of the present invention were first identified in Incyte Clone 094168 from the human pituitary gland cDNA library (PITUNOT01) using a computer search for amino acid sequence alignments. A consensus sequence, SEQ ID NO:9, was derived from the following overlapping and/or extended nucleic acid sequences: Incyte Clones 094168 (PITUNOT01), 2470694 (THP1NOT03), 3595859 (FIBPNOT01), 1864296 (PROSNOT19), 1622192 (BRAITUT13), 1695044 (COLNNOT23), and 1431642 (BEPINON01).

In one embodiment, the invention encompasses a polypeptide comprising the amino acid sequence of SEQ ID NO:1. HHLM-1 is 259 amino acids in length and has a potential glycosylation site at N47, seven potential casein kinase II phosphorylation sites at T48, S52, S68, S81, T164, T192, and S231. In addition HHLM-1 has two potential protein kinase C phosphorylation sites at T48 and T225. HHLM-1 has chemical and structural homology with $C. elegans$ 4-nitrophenylphosphatase (PPNase) (GI 1938421). In particular, HHLM-1 and PPNase share 51% identity, as well as sharing four potential phosphorylation sites and a potential glycosylation site. The fragment of SEQ ID NO:9 from about nucleotide 120 to about nucleotide 180 is useful as a hybridization probe. Northern analysis shows the expression of this sequence in neural, reproductive and cardiovascular tissue libraries, at least 61% of which are immortalized or cancerous. Of particular note is the expression of HHLM-1 in ovarian and breast tissue cancer.

Nucleic acids encoding the HHLM-2 of the present invention were first identified in Incyte Clone 195647 from the human kidney cDNA library (KIDNNOT02) using a computer search for amino acid sequence alignments. A consensus sequence, SEQ ID NO:10, was derived from the following overlapping and/or extended nucleic acid sequences: Incyte Clones 195647 (KIDNNOT02), 1795063 (PROSTUT05), 1813266 (PROSTUT12), and 728148 (SYNOOAT01).

In one embodiment, the invention encompasses a polypeptide comprising the amino acid sequence of SEQ ID NO:2. HHLM-2 is 392 amino acids in length, and has a protein phosphatase 2C signature sequence from Y147 through G155, as well as a potential glycosaminoglycan attachment site at S40. In addition, HHLM-2 has two potential glycosylation site at N87 and N382, two potential cAMP- and cGMP-dependent protein kinase phosphorylation sites at T81 and T82, twelve potential casein kinase II phosphorylation sites at S36, S55, T81, T82, T198, T263, S292, S305, T315, T333, S342, and S357, five potential protein kinase C phosphorylation sites atS13, T186, T194, S208, and S248, and two potential tyrosine kinase phosphorylation sites at Y298 and Y363. HHLM-2 has chemical and structural homology with human phosphatase 2C motif (PP2C) (GI 2114221). In particular, HHLM-2 and PP2C share 26% identity, including complete identity throughout the protein phosphatase 2C signature sequence. HHLM-2 and PP2C also share two potential phosphorylation sites and a potential glycosaminoglycan attachment site. The fragment of SEQ ID NO:10 from about nucleotide 74 to about nucleotide 134 is useful as a hybridization probe. Northern analysis shows the expression of this sequence in reproductive, neural, hematopoietic, and gastrointestinal tissue libraries, at least 43% of which are immortalized or cancerous and at least 20% of which involve inflammation and the immune response. Of particular note is the expression of HHLM-2 in brain and prostate tissue tumors.

Nucleic acids encoding the HHLM-3 of the present invention were first identified in Incyte Clone 507537 from the human blood mononuclear cell cDNA library (TMLR3DT02) using a computer search for amino acid sequence alignments. A consensus sequence, SEQ ID NO:11, was derived from the following overlapping and/or extended nucleic acid sequences: Incyte Clones 507537 (TMLR3DT02), 868893 (LUNGAST01), 2272231 (PROSNON01), 2379239 (ISLTNOT01), and 1397852 (BRAITUT08).

In one embodiment, the invention encompasses a polypeptide comprising the amino acid sequence of SEQ ID NO:3. HHLM-3 is 353 amino acids in length and has a potential cAMP- and cGMP-dependent protein kinase phosphorylation site at T265, two potential casein kinase II phosphorylation sites at S105 and S246, five potential protein kinase C phosphorylation sites at S78, T201, T272, S307, and T350, a microbodies C-terminal targeting signal at L351. HHLM-3 has chemical and structural homology with *S. cerevisiae* phosphatase (ScPPase) (GI 172168). In particular, HHLM-3 and ScPPase share 30% identity, including a potential protein kinase C phosphorylation site. The fragment of SEQ ID NO:11 from about nucleotide 72 to about nucleotide 132 is useful as a hybridization probe. Northern analysis shows the expression of this sequence in hematopoietic and immune, reproductive, and cardiovascular tissue libraries, at least 49% of which are immortalized or cancerous and at least 37% of which involve inflammation and the immune response. Of particular note is the expression of HHLM-3 in lymphocytes and a T-cell line.

Nucleic acids encoding the HHLM-4 of the present invention were first identified in Incyte Clone 971204 from the human muscle tissue cDNA library (MUSCNOT02) using a computer search for amino acid sequence alignments. A consensus sequence, SEQ ID NO:12, was derived from the following overlapping and/or extended nucleic acid sequences: Incyte Clones 971204 (MUSCNOT02), 2822470 (ADRETUT06), and shotgun sequences STEQ00223 and STEQ02003.

In one embodiment, the invention encompasses a polypeptide comprising the amino acid sequence of SEQ ID NO:4. HHLM-4 is 207 amino acids in length and has a tyrosine protein phosphatase active site signature sequence from V146 through L158. In addition, HHLM-4 has a potential glycosylation site at N93, three potential casein kinase II phosphorylation sites at T31, T128, and T170, and two potential protein kinase C phosphorylation sites at S21 and T54. HHLM-4 has chemical and structural homology with human dual-specificity protein phosphatase (tyrosine/serine) (HPPase) (GI 181840). In particular, HHLM-4 and HPPase share 37% identity, including over 90% similarity in the tyrosine specific protein phosphatases active site signature sequence. The fragment of SEQ ID NO:12 from about nucleotide 412 to about nucleotide 472 is useful as a hybridization probe. Northern analysis shows the expression of this sequence in cardiovascular, neural, and reproductive tissue libraries, at least 40% of which are immortalized or cancerous. Of particular note is the expression of HHLM-4 in ovarian cancers.

Nucleic acids encoding the HHLM-5 of the present invention were first identified in Incyte Clone 1376382 from the human lung tissue cDNA library (LUNGNOT10) using a computer search for amino acid sequence alignments. A consensus sequence, SEQ ID NO:13, was derived from the following overlapping and/or extended nucleic acid sequences: Incyte Clone 1376382 (LUNGNOT10) and shotgun sequences SAEA03372, SAEA02307, and SAEA02991.

In one embodiment, the invention encompasses a polypeptide comprising the amino acid sequence of SEQ ID NO:5. HHLM-5 is 453 amino acids in length and has seven potential glycosylation sites at N69, N131, N222, N238, N263, N356, and N437. In addition, HHLM-5 has a potential cAMP- and cGMP-dependent protein kinase phosphorylation site at S308, six potential casein kinase II phosphorylation sites at S90, S98, T294, S324, T396 and S439, a potential glycosaminoglycan attachment site at S19, seven potential protein kinase C phosphorylation sites at S64, T164, T186, S194, T294, S303, and T423, and a potential tyrosine kinase phosphorylation site at Y353. HHLM-5 has chemical and structural homology with mouse acid sphingomyelinase-like phosphodiesterase (MASP) (GI 1552350). In particular, HHLM-5 and MASP share 79% identity, including seven potential phosphorylation sites and five potential glycosylation sites. The fragment of SEQ ID NO:13 from about nucleotide 69 to about nucleotide 128 is useful as a hybridization probe. Northern analysis shows the expression of this sequence in reproductive, gastrointestinal, and hematopoietic and immune tissue libraries, at least 55% of which are immortalized or cancerous and at least 26% of which involve inflammation and the immune response. Of particular note is the expression of HHLM-5 in tumors of the prostate, uterus, testicle, and breast.

Nucleic acids encoding the HHLM-6 of the present invention were first identified in Incyte Clone 2011230 from the human testicular tissue cDNA library (TESTNOT03) using a computer search for amino acid sequence alignments. A consensus sequence, SEQ ID NO:14, was derived from the following overlapping and/or extended nucleic acid sequences: Incyte Clones 2011230 (TESTNOT03), 2855308 (CONNNOT02), 1706605 (DUODNOT02), and 1482295 and 1481157 (CORPNOT02).

In one embodiment, the invention encompasses a polypeptide comprising the amino acid sequence of SEQ ID NO:6. HHLM-6 is 270 amino acids in length and has a potential amidation site at W4, a potential glycosylation site at N55, and a glycosaminoglycan attachment site at S25. In addition, HHLM-6 has three potential casein kinase II phosphorylation sites at S60, S76, and S108, and two potential protein kinase C phosphorylation sites at S57 and T235. HHLM-6 has chemical and structural homology with *C. elegans* 4-nitrophenylphosphatase (PPNase) (GI 1938421). In particular, HHLM-6 and PPNase share 35% identity, including two potential phosphorylation sites and a potential glycosylation site. The fragment of SEQ ID NO:14 from about nucleotide 19 to about nucleotide 72 is useful as a hybridization probe. Northern analysis shows the expression of this sequence in neural, reproductive, and gastrointestinal tissue libraries, at least 47% of which are immortalized or cancerous and at least 24% of which involve inflammation and the immune response. Of particular note is the expression of HHLM-6 in tumors of the brain and ganglion.

Nucleic acids encoding the HHLM-7 of the present invention were first identified in Incyte Clone 2768301 from the human colon tissue cDNA library (COLANOT02) using a computer search for amino acid sequence alignments. A consensus sequence, SEQ ID NO:15, was derived from the following overlapping and/or extended nucleic acid sequences: Incyte Clones 2768301 (COLANOT02), 1582462 (DUODNOT01), 193790 (KIDNNOT02), 1817542 (PROSNOT20), and 1418115 (KIDNNOT09).

In one embodiment, the invention encompasses a polypeptide comprising the amino acid sequence of SEQ ID NO:7. HHLM-7 is 231 amino acids in length. HHLM-7 has a potential glycosylation site at N160, four potential casein kinase II phosphorylation sites at S18, S39, S74, and S162, and two potential protein kinase C phosphorylation sites at T46 and S162. HHLM-7 has chemical and structural homology with mouse lysophospholipase I (MLP) (GI 1864159). In particular, HHLM-7 and MLP share 65% identity. The fragment of SEQ ID NO:15 from about nucleotide 113 to about nucleotide 166 is useful as a hybridization probe. Northern analysis shows the expression of this sequence in reproductive, gastrointestinal, and developmental tissue libraries, at least 60% of which are immortalized or cancerous and at least 22% of which involve the inflammatory response. Of particular note is the expression of HHLM-7 in tumors of the breast and prostate.

Nucleic acids encoding the HHLM-8 of the present invention were first identified in Incyte Clone 2886583 from the human jejunum tissue cDNA library (SINJNOT02) using a computer search for amino acid sequence alignments. A consensus sequence, SEQ ID NO:16, was derived from the following overlapping and/or extended nucleic acid sequences: Incyte Clones 2886583 (SINJNOT02), 1666224 (BRSTNOT09), and 1223154 (COLNTUT02).

In one embodiment, the invention encompasses a polypeptide comprising the amino acid sequence of SEQ ID NO:8. HHLM is 254 amino acids in length and has four potential casein kinase II phosphorylation sites at S177, S203, T204, and S218, and two potential protein kinase C phosphorylation sites at S14 and S119. HHLM-8 has chemical and structural homology with A. thaliana glyoxylase II (AGLX) (GI 1644427). In particular, HHLM and AGLX share 57% identity, including a potential phosphorylation site. The fragment of SEQ ID NO:16 from about nucleotide 66 to about nucleotide 123 is useful as a hybridization probe. Northern analysis shows the expression of this sequence in gastrointestinal and reproductive tissue libraries, at least 69% of which are immortalized or cancerous and at least 26% of which involve inflammation and the immune response. Of particular note is the expression of HHLM in tumors of the prostate and colon.

The invention also encompasses HHLM variants. A preferred HHLM variant is one which has at least about 80%, more preferably at least about 90%, and most preferably at least about 95% amino acid sequence identity to the HHLM amino acid sequence, and which contains at least one functional or structural characteristic of HHLM.

The invention also encompasses polynucleotides which encode HHLM. In a particular embodiment, the invention encompasses a polynucleotide sequence comprising a polynucleotide sequence selected from the group consisting of SEQ ID NO:9, SEQ ID NO:10, SEQ ID NO:11, SEQ ID NO:12, SEQ ID NO:13, SEQ ID NO:14, SEQ ID NO:15, and SEQ ID NO:16, which encode HHLM.

The invention also encompasses a variant of a polynucleotide sequence encoding HHLM. In particular, such a variant polynucleotide sequence will have at least about 80%, more preferably at least about 90%, and most preferably at least about 95% polynucleotide sequence identity to the polynucleotide sequence encoding HHLM. A particular aspect of the invention encompasses a variant of SEQ ID NO:9 which has at least about 80%, more preferably at least about 90%, and most preferably at least about 95% polynucleotide sequence identity to SEQ ID NO:9. The invention further encompasses a polynucleotide variant of SEQ ID NO:10 having at least about 80%, preferably at least about 90%, and most preferably at least about 95% polynucleotide sequence identity to SEQ ID NO:10. The invention further encompasses a polynucleotide variant of SEQ ID NO:11 having at least about 80%, preferably at least about 90%, and most preferably at least about 95% polynucleotide sequence identity to SEQ ID NO:11. The invention further encompasses a polynucleotide variant of SEQ ID NO:12 having at least about 80%, preferably at least about 90%, and most preferably at least about 95% polynucleotide sequence identity to SEQ ID NO:12. The invention further encompasses a polynucleotide variant of SEQ ID NO:13 having at least about 80%, preferably at least about 90%, and most preferably at least about 95% polynucleotide sequence identity to SEQ ID NO:13. The invention further encompasses a polynucleotide variant of SEQ ID NO:14 having at least about 80%, preferably at least about 90%, and most preferably at least about 95% polynucleotide sequence identity to SEQ ID NO:14. The invention further encompasses a polynucleotide variant of SEQ ID NO:15 having at least about 80%, preferably at least about 90%, and most preferably at least about 95% polynucleotide sequence identity to SEQ ID NO:15. The invention further encompasses a polynucleotide variant of SEQ ID NO:16 having at least about 80%, preferably at least about 90%, and most preferably at least about 95% polynucleotide sequence identity to SEQ ID NO:16. Any one of the polynucleotide variants described above can encode an amino acid sequence which contains at least one functional or structural characteristic of HHLM.

It will be appreciated by those skilled in the art that as a result of the degeneracy of the genetic code, a multitude of polynucleotide sequences encoding HHLM, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HHLM, and all such variations are to be considered as being specifically disclosed.

Although nucleotide sequences which encode HHLM and its variants are preferably capable of hybridizing to the nucleotide sequence of the naturally occurring HHLM under appropriately selected conditions of stringency, it may be advantageous to produce nucleotide sequences encoding HHLM or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HHLM and its derivatives without altering the encoded amino acid sequences include the production of RNA transcripts having more desirable properties, such as a greater half-life, than transcripts produced from the naturally occurring sequence.

The invention also encompasses production of DNA sequences which encode HHLM and HHLM derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HHLM or any fragment thereof.

Also encompassed by the invention are polynucleotide sequences that are capable of hybridizing to the claimed polynucleotide sequences, and, in particular, to those shown in SEQ ID NO:9, SEQ ID NO:10, SEQ ID NO:11, SEQ ID NO:12, SEQ ID NO:13, SEQ ID NO:14, SEQ ID NO:15, SEQ ID NO:16, a fragment of SEQ ID NO:9, a fragment of SEQ ID NO:10, a fragment of SEQ ID NO:11, a fragment of SEQ ID NO:12, a fragment of SEQ ID NO:13, a fragment of SEQ ID NO:14, a fragment of SEQ ID NO:15, or a fragment of SEQ ID NO:16 under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, T7SEQUENASE DNA polymerase (Amersham Pharbacia Biotech, Piscataway, N.J.), Taq DNA polymerase (Perkin Elmer), THERMOSEQUENASE CNA polymerase (Amersham Pharmacia Biotech), or combinations of polymerases and proofreading exonucleases such as those found in the ELONGASE amplification system (Life Technologies, Gaithersburg, Md.). Preferably, the process is automated with machines such as the MICROLAB 2200 SYSTEM (Hamilton, Reno, Nev.), DNA ENGINE Thermal cycler (PTC200; MJ Research, Watertown, Mass.) and the ABI CATALYST, ABI PRISM 373, ABI PRISM 377 sequencing systems (PE Biosystems, Foster City, Cailf.

The nucleic acid sequences encoding HHLM may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR and nested primers to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length CDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR analysis sofrware, PE Biosystems), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HHLM may be used in recombinant DNA molecules to direct expression of HHLM, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HHLM.

As will be understood by those of skill in the art, it may be advantageous to produce HHLM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HHLM-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HHLM may be ligated to a heterologous sequence to encode a fusion protein. For example, to screen peptide libraries for inhibitors of HHLM activity, it may be useful to encode a chimeric HHLM protein that can be recognized by a commercially available antibody. A fusion protein may also be engineered to contain a cleavage site located between the HHLM encoding sequence and the heterologous protein sequence, so that HHLM may be cleaved and purified away from the heterologous moiety.

In another embodiment, sequences encoding HHLM may be synthesized, in whole or in part, using chemical methods well known in the art. (See, e.g., Caruthers, M. H. et al. (1980) Nucl. Acids Symp. Ser. (7)215–223, and Horn, T. et al. (1980) Nucl. Acids Res. Symp. Ser. (7)225–232.) Alternatively, the protein itself may be produced using chemical methods to synthesize the amino acid sequence of HHLM, or a fragment thereof. For example, peptide synthesis can be performed using various solid-phase techniques. (See, e.g., Roberge, J. Y. et al. (1995) Science 269:202–204.) Automated synthesis may be achieved using the ABI Model 431A peptide Synthesizer (PE Biosystems). Additionally, the amino acid sequence of HHLM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular properties*, WH Freeman and Co., New York, N.Y.)

In order to express a biologically active HHLM, the nucleotide sequences encoding HHLM or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HHLM and appropriate transcriptional and translational control elements. These methods include in vitro recombinant DNA techniques, synthetic techniques, and in vivo genetic recombination. (See, e.g., Sambrook, J. et al. (1989) *Molecular Cloning A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HHLM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HHLM which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla, Calif.) or PSPORT1 plasmid (Life Technologies), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HHLM, vectors based on SV40 or EBV may be used with an appropriate selectable marker.

In bacterial systems, a number of expression vectors may be selected depending upon the use intended for HHLM. For example, when large quantities of HHLM are needed for the induction of antibodies, vectors which direct high level expression of fusion proteins that are readily purified may be used. Such vectors include, but are not limited to, multifunctional *E. coli* cloning and expression vectors such as BLUESCIPT (Stratagene), in which the sequence encoding HHLM may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) PGEX vectors (Amersham Pharmacia Biotech) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HHLM may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HHLM. For example, in one such system, *Autographa californica* nuclear polyhedrosis virus (AcNPV) is used as a vector to express foreign genes in *Spodoptera frugiperda* cells or in Trichoplusia larvae. The sequences encoding HHLM may be cloned into a non-essential region of the virus, such as the polyhedrin gene, and placed under control of the polyhedrin promoter. Successful insertion of sequences encoding HHLM will render the polyhedrin gene inactive and produce recombinant virus lacking coat protein. The recombinant viruses may then be used to infect, for example, *S. frugiperda* cells or Trichoplusia larvae in which HHLM may be expressed. (See, e.g., Engelhard, E. K. et al. (1994) Proc. Natl. Acad. Sci. 91:3224–3227.)

In mammalian host cells, a number of viral-based expression systems may be utilized. In cases where an adenovirus is used as an expression vector, sequences encoding HHLM may be ligated into an adenovirus transcription/translation complex consisting of the late promoter and tripartite leader sequence. Insertion in a non-essential E1 or E3 region of the viral genome may be used to obtain a viable virus which is capable of expressing HHLM in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HHLM. Such signals include the ATG initiation codon and adjacent sequences. In cases where sequences encoding HHLM and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HHLM can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in $tk^-$ or $apr^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HHLM is inserted within a marker gene sequence, transformed cells containing sequences encoding HHLM can be identified by the absence of marker gene function. Alternatively, a marker gene can be placed in tandem with a sequence encoding HHLM under the control of a single promoter. Expression of the marker gene in response to induction or selection usually indicates expression of the tandem gene as well.

Alternatively, host cells which contain the nucleic acid sequence encoding HHLM and express HHLM may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HHLM can be detected by DNA-DNA or DNA-RNA hybridization or amplification using probes or fragments or fragments of polynucleotides encoding HHLM. Nucleic acid amplification based assays involve the use of oligonucleotides or oligomers based on the sequences encoding HHLM to detect transformants containing DNA or RNA encoding HHLM.

A variety of protocols for detecting and measuring the expression of HHLM, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HHLM is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HHLM include oligolabeling, nick translation, end-labeling, or PCR amplification using a labeled nucleotide. Alternatively, the sequences encoding HHLM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amershan Pharmacia Bistech and, Promega (Madison, Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HHLM may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HHLM may be designed to contain signal sequences which direct secretion of HHLM through a prokaryotic or eukaryotic cell membrane. Other constructions may be used to join sequences encoding HHLM to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HHLM encoding sequence may be used to facilitate purification. One such expression vector provides for expression of a fusion protein containing HHLM and a nucleic acid encoding 6 histidine residues preceding a thioredoxin or an enterokinase cleavage site. The histidine residues facilitate purification on immobilized metal ion affinity chromatography (IMAC). (See, e.g., Porath, J. et al. (1992) Prot. Exp. Purif. 3:263–281.) The enterokinase cleavage site provides a means for purifying HHLM from the fusion protein. (See, e.g., Kroll, D. J. et al. (1993) DNA Cell Biol. 12:441–453.) Fragments of HHLM may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the ABI model 431A peptide synthesizer (PE Biosystems). Various fragments of HHLM may be synthesized separately and then combined to produce the full length molecule.

Therapeutics

Chemical and structural homology exists among the human hydrolase-like molecules of the invention. In addition, HHLM is expressed in cancerous or immortalized tissues and tissues associated with inflammation and the autoimmune response. There fore, HHLM appears to play a role in cell proliferation disorders, and autoimmune disorders.

Therefore, in one embodiment, an antagonist of HHLM may be administered to a subject to treat or prevent a cell proliferation disorder. Such a disorder may include, but is not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HHLM may be used directly as an antagonist or indirectly as a targeting or delivery mechanism for bringing a pharmaceutical agent to cells or tissue which express HHLM.

In an additional embodiment, a vector expressing the complement of the polynucleotide encoding HHLM may be administered to a subject to treat or prevent a cell proliferation disorder including, but not limited to, those described above.

In a further embodiment, an antagonist of HHLM may be administered to a subject to treat or prevent an autoimmune disorder. Such a disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In an additional embodiment, a vector expressing the complement of the polynucleotide encoding HHLM may be administered to a subject to treat or prevent an autoimmune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HHLM may be produced using methods which are generally known in the art. In particular, purified HHLM may be used to produce antibodies or to screen libraries of pharmaceutical agents to identify those which specifically bind HHLM. Antibodies to HHLM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HHLM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HHLM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HHLM amino acids may be fused with those of another protein, such as KLH, and antibodies to the chimeric molecule may be produced.

Monoclonal antibodies to HHLM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HHLM-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; and Winter, G. et al. (1991) Nature 349:293–299.) Antibody fragments which contain specific binding sites for HHLM may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HHLM and its specific antibody. A two-site, monoclonal-based immunoassay utilizing monoclonal antibodies reactive to two non-interfering HHLM epitopes is preferred, but a competitive binding assay may also be employed. (Maddox, supra.)

In another embodiment of the invention, the polynucleotides encoding HHLM, or any fragment or complement thereof, may be used for therapeutic purposes. In one aspect, the complement of the polynucleotide encoding HHLM may be used in situations in which it would be desirable to block the transcription of the mRNA. In particular, cells may be transformed with sequences complementary to polynucleotides encoding HHLM. Thus, complementary molecules or fragments may be used to modulate HHLM activity, or to achieve regulation of gene function. Such technology is now well known in the art, and sense or antisense oligonucleotides or larger fragments can be designed from various locations along the coding or control regions of sequences encoding HHLM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HHLM. (See, e.g., Sambrook, supra; and Ausubel, supra.)

Genes encoding HHLM can be turned off by transforming a cell or tissue with expression vectors which express high levels of a polynucleotide, or fragment thereof, encoding HHLM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HHLM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HHLM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HHLM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HHLM, antibodies to HHLM, and mimetics, agonists, antagonists, or inhibitors of HHLM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HHLM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HHLM or fragments thereof, antibodies of HHLM, and agonists, antagonists or inhibitors of HHLM, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of therapeutic to toxic effects is the therapeutic index, and it can be expressed as the LDSO/EDSO ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HHLM may be used for the diagnosis of disorders characterized by expression of HHLM, or in assays to monitor patients being treated with HHLM or agonists, antagonists, or inhibitors of HHLM. Antibodies useful for diagnostic purposes may be prepared in the same manner as described above for therapeutics. Diagnostic assays for HHLM include methods which utilize the antibody and a label to detect HHLM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HHLM, including ELISAs, RIAs, and FACS, are known in the art and provide a basis for diagnosing altered or abnormal levels of HHLM expression. Normal or standard values for HHLM expression are established by combining body fluids or cell extracts taken from normal mammalian subjects, preferably human, with antibody to HHLM under conditions suitable for complex formation The amount of standard complex formation may be quantitated by various methods, preferably by photometric means. Quantities of HHLM expressed in subject, control, and disease samples from biopsied tissues are compared with the standard values. Deviation between standard and subject values establishes the parameters for diagnosing disease.

In another embodiment of the invention, the polynucleotides encoding HHLM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HHLM may be correlated with disease. The diagnostic assay may be used to determine absence, presence, and excess expression of HHLM, and to monitor regulation of HHLM levels during therapeutic intervention.

In one aspect, hybridization with PCR probes which are capable of detecting polynucleotide sequences, including genomic sequences, encoding HHLM or closely related molecules may be used to identify nucleic acid sequences which encode HHLM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HHLM, alleles, or related sequences.

Probes may also be used for the detection of related sequences, and should preferably have at least 50% sequence identity to any of the HHLM encoding sequences. The hybridization probes of the subject invention may be DNA or RNA and may be derived from the sequence SEQ ID NO:9, SEQ ID NO:10, SEQ ID NO:11, SEQ ID NO:12, SEQ ID NO:13, SEQ ID NO:14, SEQ ID NO:15, SEQ ID NO:16, or from genomic sequences including promoters, enhancers, and introns of the HHLM gene.

Means for producing specific hybridization probes for DNAs encoding HHLM include the cloning of polynucleotide sequences encoding HHLM or HHLM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HHLM may be used for the diagnosis of a disorder associated with expression of HHLM. Examples of such a disorder include, but are not limited to, cell proliferation disorders such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and autoimmune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HHLM may be used in Southern or northern analysis, dot blot, or other membrane-based technologies; in PCR technologies; in dipstick, pin, and ELISA-like assays; and in microarrays utilizing fluids or tissues from patients to detect altered HHLM expression. Such qualitative or quantitative methods are well known in the art.

In a particular aspect, the nucleotide sequences encoding HHLM may be useful in assays that detect the presence of associated disorders, particularly those mentioned above. The nucleotide sequences encoding HHLM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HHLM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HHLM, a normal or standard profile for expression is established. This may be accomplished by combining body fluids or cell extracts taken from normal subjects, either animal or human, with a sequence, or a fragment thereof, encoding HHLM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

Additional diagnostic uses for oligonucleotides designed from the sequences encoding HHLM may involve the use of PCR. These oligomers may be chemically synthesized, generated enzymatically, or produced in vitro. Oligomers will preferably contain a fragment of a polynucleotide encoding HHLM, or a fragment of a polynucleotide complementary to the polynucleotide encoding HHLM, and will be employed under optimized conditions for identification of a specific gene or condition. Oligomers may also be employed under less stringent conditions for detection or quantitation of closely related DNA or RNA sequences.

Methods which may also be used to quantitate the expression of HHLM include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Chee et al. (1995) PCT application WO95/11995; Fodor, S.P.A. et al. (1995) U.S. Pat. No. 5,424,186; Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Lockhart, D. J. et al. (1996) Nat. Biotech. 14:1675–1680; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HHLM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HHLM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HHLM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HHLM and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HHLM, or fragments thereof, and washed. Bound HHLM is then detected by methods well known in the art. Purified HHLM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HHLM specifically compete with a test compound for binding HHLM. In this manner, antibodies can be used to detect the presence of any peptide which shares one or more antigenic determinants with HHLM.

In additional embodiments, the nucleotide sequences which encode HHLM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the LUNGNOT10 cDNA library, from which Incyte Clone 1376382 was isolated, is described. Preparation and sequencing of cDNAs in libraries in the LIFESEQ database (Incyte Phamaceuticals, Inc., Palo Alto, Cailf.) have varied over time, and the gradual changes involved use of kits, plasmids, and machinery available at the particular time the library was made and analyzed.

LUNGNOT10 cDNA Library Construction

The LUNGNOT10 cDNA library was constructed from normal lung tissue obtained from a 23-week-old Caucasian male fetus. The frozen tissue was homogenized and lysed using a POLYTRON homgerizer (PT-3000; (Brinkmann Instruments, Westbury, N.J.) in guanidinium isothiocyanate solution. The lysate was centrifuged over a 5.7 M CsCl cushion using Beckman SW28 rotor in a Beckman L8-70M Ultracentrifuge (Beckman Coulter Fullerton, Cailf. for 18 hours at 25,000 rpm at ambient temperature. The RNA was extracted with acid phenol pH 4.0, precipitated using 0.3 M sodium acetate and 2.5 volumes of ethanol, resuspended in RNAse-free water, and DNase treated at 37° C. RNA extraction and precipitation were repeated as before. The mRNA was then isolated using the OLIGOTEX kit (QIAGEN, Inc., Chatsworth, Calif.) and used to construct the cDNA library.

The mRNA was handled according to the recommended protocols in the SUPERSCRIPT plasmid system (Life Tedhnologies. cDNAs were fractionated on a SEPHAROSE CL4B column (Amersham Pharmacia Bectech, and those cDNAs exceeding 400 bp were ligated into pINCY I. The plasmid pINCY I plasmid (Incyte Pharmaceuticals) was subsequently transformed into DH5a competent cells (Life Technologies.

II Isolation and Sequencing of cDNA Clones

Plasmid DNA was released from the cells and purified using the REAL Prep 96 plasmid kit (QIAGEN, Inc.). This kit enabled the simultaneous purification of 96 samples in a 96-well block using multi-channel reagent dispensers. The recommended protocol was employed except for the following changes:1) the bacteria were cultured in 1 ml of sterile Terrific Broth (Life Technologies) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2000 system (Hamilton) in combination with the DNA ENGINE thermal cycler (MJ Research) and sequenced using ABI PRISM 377 sequencing system (PE Biosystems); and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HHLM occurs. Abundance and percent abundance are also reported. Abundance directly reflects the number of times a particular transcript is represented in a cDNA library, and percent abundance is abundance divided by the total number of sequences examined in the cDNA library.

V. Extension of HHLM Encoding Polynucleotides

The nucleic acid sequences of Incyte Clones 094168, 195647, 507537, 971204, 1376382, 2011230, 2768301, and 2886583 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 primer analysis software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (DNA ENGINE thermal cycler (MJ Research)), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK kit (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent *E. coli* cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2×Carb. The following day, several colonies were randomly picked from each plate and cultured in 150 µl of liquid LB/2× Carb medium placed in an individual well of an appropriate commercially-available sterile 96-well microtiter plate. The following day, 5 µl of each overnight culture was transferred into a non-sterile 96-well plate and, after dilution 1: 10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:9, SEQ ID NO:10, SEQ ID NO:11, SEQ ID NO:12, SEQ ID NO:13, SEQ ID NO:14, SEQ ID NO:15, and SEQ ID NO:16 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:9, SEQ ID NO:10, SEQ ID NO:11, SEQ ID NO:12, SEQ ID NO:13, SEQ ID NO:14, SEQ ID NO:15, and SEQ ID NO:16 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06. primer analysis software (National Biosciences) and labeled by combining 50 pmol of each oligomer, 250 µCi of [$\gamma$-$^{32}$P] adenosine triphosphate (Amersham Pharmacia Biotech), and T4 polynucleotide kinase (NEN Life Science Products, Boston, Mass.). The labeled oligonucleotides are substantially purified using a SEPHADEX G-25 superfine resin column (Amershal Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (NEN Life Science Products).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots to film for several hours, hybridization patterns are compared visually.

VII. Microarrays To produce oligonucleotides for a microarray, one of the nucleotide sequences of the present invention is examined using a computer algorithm which starts at the 3' end of the nucleotide sequence. For each, the algorithm identifies oligomers of defined length that are unique to the nucleic acid sequence, have a GC content within a range suitable for hybridization, and lack secondary structure that would interfere with hybridization. The algorithm identifies approximately 20 oligonucleotides corresponding to each nucleic acid sequence. For each sequence-specific oligonucleotide, a pair of oligonucleotides is synthesized in which the first oligonucleotides differs from the second oligonucleotide by one nucleotide in the center of the sequence. The oligonucleotide pairs can be arranged on a substrate, e.g. a silicon chip, using a light-directed chemical process. (See, e.g., Chee, supra.)

Probe sequences may be selected by screening a large number of clones from a variety of cDNA libraries in order to find sequences with conserved protein motifs common to genes coding for signal sequence containing polypeptides. In one embodiment, sequences identified from cDNA libraries, are analyzed to identify those gene sequences with conserved protein motifs using an appropriate analysis program, e.g., the Block 2.bioanalysis program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify functional or structural domains that cannot be detected using conserved motifs due to extreme sequence divergence. The method is based on weight matrices. Motifs identified by this method are then calibrated against the SWISS-PROT database in order to obtain a measure of the chance distribution of the matches.

In another embodiment, Hidden Markov models (HMMs) may be used to find shared motifs, specifically consensus sequences. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

In the alternative, a chemical coupling procedure and an ink jet device can be used to synthesize oligomers on the surface of a substrate. (See, e.g., Baldeschweiler, supra.) An array analogous to a dot or slot blot may also be used to arrange and link fragments or oligonucleotides to the surface of a substrate using or thermal, UV, mechanical, or chemical bonding procedures, or a vacuum system. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each oligonucleotide sequence on the microarray may be assessed through analysis of the scanned images.

In another alternative, full-length cDNAs or Expressed Sequence Tags (ESTs) comprise the elements of the microarray. Full-length cDNAs or ESTs corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed, by thermal and chemical and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HHLM-encoding sequences, or any parts thereof, are used to detect, decrease, or inhibit expression of naturally occurring HHLM. Although use of oligonucleotides comprising from about 15 to 30 base pairs is described, essentially the same procedure is used with smaller or with larger sequence fragments. Appropriate oligonucleotides are designed using OLIGO 4.06 primer analysis software (National Bioscienses) and the coding sequence of HHLM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HHLM-encoding transcript.

IX. Expression of HHLM

Expression of HHLM is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HHLM into bacterial growth media which can be used directly in the following assay for activity.

X. Demonstration of HHLM Activity

For purposes of example, an assay measuring the phosphatase activity of an HHLM molecule is described. Varying amounts of HHLM are incubated with a fixed amount of [$^{32}$P]-labeled myelin basic protein (MBP). After incubation under appropriate conditions of time, temperature, pH, and ionic strength described by Li, M. et al. (1995, Biochemistry 34:1988–1996), the proteins are precipitated with cold trichloroacetic acid and collected on nitrocellulose filters with a 0.45$\mu$ pore size (Millipore, Bedford, Mass.). The filters are dried and immersed in a commercially available scintillation fluid prior to counting in a scintillation counter (Beckman coulter). The amount of [$^{32}$P]phosphate released from MBP by HHLM is proportional to the activity of HHLM in the sample.

XI. Production of HHLM Specific Antibodies

HHLM substantially purified using PAGE electrophoresis (see, e.g., Harrington, M. G. (1990) Methods Enzymol. 182:488–495), or other purification techniques, is used to immunize rabbits and to produce antibodies using standard protocols. The HHLM amino acid sequence is analyzed using LASERGENE software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an ABI Model 431A peptide synthesizer (PE Biosystem) using Fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HHLM Using Specific Antibodies

Naturally occurring or recombinant HHLM is substantially purified by immunoaffinity chromatography using antibodies specific for HHLM. An immunoaffinity column is constructed by covalently coupling anti-HHLM antibody to an activated chromatographic resin, such as CNBr-activated SEPHAROSE (Amersham Pharmacia Brothech). After the coupling, the resin is blocked and washed according to the manufacturer's instructions.

Media containing HHLM are passed over the immunoaffinity column, and the column is washed under conditions that allow the preferential absorbance of HHLM (e.g., high ionic strength buffers in the presence of detergent). The column is eluted under conditions that disrupt antibody/HHLM binding (e.g., a buffer of pH 2 to pH 3, or a high concentration of a chaotrope, such as urea or thiocyanate ion), and HHLM is collected.

XIII. Identification of Molecules Which Interact with HHLM

HHLM, or biologically active fragments thereof, are labeled with $^{125}$I Bolton-Hunter reagent. (See, e.g., Bolton et al. (1973) Biochem. J. 133:529 (hyphen)-539.) Candidate molecules previously arrayed in the wells of a multi-well plate are incubated with the labeled HHLM, washed, and any wells with labeled HHLM complex are assayed. Data obtained using different concentrations of HHLM are used to calculate values for the number, affinity, and association of HHLM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified cDNA encoding a polypeptide selected from SEQ ID NOs:1–8.

2. An isolated and purified polynucleotide variant having at least 90% polynucleotide sequence identity over the full length of the cDNA of claim 1.

3. A probe comprising the cDNA of claim 1.

4. An isolated and purified polynucleotide having a sequence which is fully complementary to the cDNA of claim 1.

5. An isolated and purified polynucleotide comprising a polynucleotide sequence selected from the group consisting of SEQ ID NOs:9–16.

6. An isolated and purified polynucleotide variant having at least 90% polynucleotide sequence identity over the full length of the polynucleotide of claim 5.

7. An isolated and purified polynucleotide having a sequence which is fully complementary to the polynucleotide of claim 5.

8. An expression vector containing the cDNA of claim 1.

9. A host cell containing the expression vector of claim 8.

10. A method for producing a polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, a fragment of SEQ ID NO:7, and a fragment of SEQ ID NO:8, the method comprising the steps of:

a) culturing the host cell of claim 9 under conditions suitable for the expression of the polypeptide; and b) recovering the polypeptide from the host cell culture.

11. A method for detecting a polynucleotide encoding the polypeptide comprising the amino acid sequence selected from the group consisting of SEQ ID NOs:1–8 in a biological sample, the method comprising the steps of:

(a) hybridizing the polynucleotide of claim 2 to at least one of the nucleic acids in the biological sample, thereby forming a hybridization complex; and (b) detecting the hybridization complex, wherein the presence of the hybridization complex correlates with the presence of the polynucleotide encoding the polypeptide in the biological sample.

12. The method of claim 11 wherein the nucleic acids of the biological sample are amplified by the polymerase chain reaction prior to hybridization.

13. A method of using a polynucleotide to screen a library of molecules to identify at least one molecule which specifically binds the polynucleotide, the method comprising the steps of:

a) combining a polynucleotide consisting of the cDNA of claim 1 with a library of molecules under conditions to allow specific binding, and b) detecting specific binding, thereby identifying a molecule which specifically binds the polynucleotide.

14. The method of claim 13 wherein the library is selected from DNA molecules, RNA molecules, peptide nucleic acids, transcription factors, and artificial chromosome constructions.

15. A method of using a polynucleotide to purify a molecule from a sample which specifically binds the polynucleotide, the method comprising:

a) combining the cDNA of claim 1 with molecules in the sample under conditions to allow specific binding;

b) recovering the bound cDNA; and c) separating the cDNA from the molecule, thereby obtaining purified molecule.

16. A probe of about 100 nucleotides in length comprising a contiguous fragment of nucleotides 1 through 45 of any one of SEQ ID NOs:9–16 or the complement thereof.

17. A cDNA probe comprising 674 contiguous nucleotides of nucleotides 1 through 674 of any one of SEQ ID NOs:9–16 or the complement thereof.

\* \* \* \* \*